(12) United States Patent
Hubbell

(10) Patent No.: US 10,704,164 B2
(45) Date of Patent: *Jul. 7, 2020

(54) METHODS, SYSTEMS, COMPUTER READABLE MEDIA, AND KITS FOR SAMPLE IDENTIFICATION

(75) Inventor: Earl Hubbell, Palo Alto, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 709 days.

This patent is subject to a terminal disclaimer.

(21) Appl. No.: 13/599,876

(22) Filed: Aug. 30, 2012

(65) Prior Publication Data

US 2013/0053256 A1 Feb. 28, 2013

Related U.S. Application Data

(60) Provisional application No. 61/545,290, filed on Oct. 10, 2011, provisional application No. 61/529,687, filed on Aug. 31, 2011.

(51) Int. Cl.
| | |
|---|---|
| *C40B 20/04* | (2006.01) |
| *C40B 50/16* | (2006.01) |
| *C40B 70/00* | (2006.01) |
| *G16B 30/00* | (2019.01) |

(52) U.S. Cl.
CPC .............. *C40B 20/04* (2013.01); *C40B 50/16* (2013.01); *C40B 70/00* (2013.01); *B01J 2219/00317* (2013.01); *B01J 2219/00466* (2013.01); *B01J 2219/00547* (2013.01); *B01J 2219/00572* (2013.01); *B01J 2219/00653* (2013.01); *G16B 30/00* (2019.02)

(58) Field of Classification Search
None
See application file for complete search history.

(56) References Cited

U.S. PATENT DOCUMENTS

| | | | |
|---|---|---|---|
| 2,632,058 A | 3/1953 | Gray | |
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,210,015 A | 5/1993 | Gelfand et al. | |
| 5,399,491 A | 3/1995 | Kacian et al. | |
| 5,750,341 A | 5/1998 | Macevicz | |
| 5,854,033 A | 12/1998 | Lizardi | |
| 6,172,214 B1 | 1/2001 | Brenner | |
| 6,174,670 B1 | 1/2001 | Wittwer et al. | |
| 6,210,891 B1 | 4/2001 | Nyren et al. | |
| 6,235,475 B1 | 5/2001 | Brenner et al. | |
| 6,251,639 B1 | 6/2001 | Kurn | |
| 6,258,568 B1 | 7/2001 | Nyren | |
| 6,274,320 B1 | 8/2001 | Rothberg et al. | |
| 6,404,907 B1 | 6/2002 | Gilchrist et al. | |
| 6,780,591 B2 | 8/2004 | Williams et al. | |
| 6,828,100 B1 | 12/2004 | Ronaghi | |
| 6,833,246 B2 | 12/2004 | Balasubramanian | |
| 6,911,327 B2 | 6/2005 | McMillan et al. | |
| 7,037,687 B2 | 5/2006 | Williams et al. | |
| 7,049,645 B2 | 5/2006 | Sawada et al. | |
| 7,117,095 B2 | 10/2006 | Hubbell | |
| 7,133,782 B2 | 11/2006 | Odedra | |
| 7,211,390 B2 | 5/2007 | Rothberg et al. | |
| 7,244,559 B2 | 7/2007 | Rothberg et al. | |
| 7,264,929 B2 | 9/2007 | Rothberg et al. | |
| 7,323,305 B2 | 1/2008 | Leamon et al. | |
| 7,323,309 B2 | 1/2008 | Mirkin et al. | |
| 7,335,762 B2 | 2/2008 | Rothberg et al. | |
| 7,348,181 B2 | 3/2008 | Walt et al. | |
| 7,424,371 B2 | 9/2008 | Kamentsky | |
| 7,535,232 B2 | 5/2009 | Barbaro et al. | |
| 7,575,865 B2 | 8/2009 | Leamon et al. | |
| 7,645,596 B2 | 1/2010 | Williams et al. | |
| 7,695,907 B2 | 4/2010 | Miyahara et al. | |
| 7,782,237 B2 | 8/2010 | Ronaghi et al. | |
| 7,785,862 B2 | 8/2010 | Kim et al. | |
| 7,835,871 B2 | 11/2010 | Kain et al. | |
| 7,838,226 B2 | 11/2010 | Kamahori et al. | |

(Continued)

FOREIGN PATENT DOCUMENTS

| | | |
|---|---|---|
| EP | 2053132 A1 | 4/2009 |
| GB | 2461127 | 12/2009 |

(Continued)

OTHER PUBLICATIONS

Baicheva, "Binary and ternary linear codes which are good and proper for error correction," Institute of Mathematics and Informatics, Bulgarian Academy of Sciences, pp. 1-6, available at http://www.moi.math.bas.bg/~tsonka/ACCT.pdf (last visited Oct. 22, 2013).
Brenner et al., "Encoded combinatorial chemistry," *Proc. Natl. Acad. Sci. USA*, 89:5381-5383 (1992).
Lee, "Some Properties of Nonbinary Error-Correcting Codes," *IRE Transactions on Information Theory*, 77-82 (1958).
Qiu et al., "DNA Sequence-Based 'Bar Codes' for Tracking the Origins of Expressed Sequence Tags from a Maize cDNA Library Constructed Using Multiple mRNA Sources," *Plant Physiol.*, 133 :475-481 (2003).
Schwartz et al., "The Structure of Single-Track Gray Codes," *IEEE Transactions on Information Theory*, 45(7):2383-2396 (1999).

(Continued)

*Primary Examiner* — Joseph Woitach
(74) *Attorney, Agent, or Firm* — Jones Robb, PLLC

(57) ABSTRACT

A method for sequencing a polynucleotide sample having a barcode sequence, includes: introducing a series of nucleotides to the polynucleotide sample according to a predetermined flow ordering; obtaining a series of signals resulting from the introducing of nucleotides to the polynucleotide sample; and resolving the series of signals over the barcode sequence to render a flowspace string, wherein the flowspace string is a codeword of an error-tolerant code capable of distinguishing the barcode sequence from other barcode sequences in the presence of one or more errors.

20 Claims, 16 Drawing Sheets

Specification includes a Sequence Listing.

(56) References Cited

U.S. PATENT DOCUMENTS

| | | | |
|---|---|---|---|
| 7,867,703 | B2 | 1/2011 | Sampson et al. |
| 7,875,440 | B2 | 1/2011 | Williams et al. |
| 7,888,013 | B2 | 2/2011 | Miyahara et al. |
| 7,948,015 | B2 | 5/2011 | Rothberg et al. |
| 8,058,055 | B2 | 11/2011 | Barrett et al. |
| 8,202,691 | B2 | 6/2012 | Steemers et al. |
| 8,262,900 | B2 | 9/2012 | Rothberg et al. |
| 8,306,757 | B2 | 11/2012 | Rothberg et al. |
| 8,309,307 | B2 | 11/2012 | Barrett et al. |
| 8,568,979 | B2 | 10/2013 | Stuelpnagel et al. |
| 8,673,627 | B2 | 3/2014 | Noble et al. |
| 2003/0219797 | A1 | 11/2003 | Zhao et al. |
| 2003/0232348 | A1 | 12/2003 | Jones et al. |
| 2004/0018506 | A1 | 1/2004 | Koehler et al. |
| 2004/0197793 | A1 | 10/2004 | Hassibi et al. |
| 2004/0197845 | A1 | 10/2004 | Hassibi et al. |
| 2005/0084851 | A1 | 4/2005 | Ronaghi et al. |
| 2006/0147935 | A1 | 7/2006 | Linnarsson |
| 2006/0147983 | A1 | 7/2006 | O'uchi et al. |
| 2007/0059733 | A1 | 3/2007 | Sundararajan et al. |
| 2007/0059741 | A1 | 3/2007 | Kamahori et al. |
| 2007/0092872 | A1 | 4/2007 | Rothberg et al. |
| 2007/0207471 | A1 | 9/2007 | Osaka et al. |
| 2007/0219367 | A1 | 9/2007 | Shchepinov et al. |
| 2007/0281300 | A1 | 12/2007 | Russell et al. |
| 2008/0166727 | A1 | 7/2008 | Esfandyarpour et al. |
| 2008/0182757 | A1 | 7/2008 | Heiner et al. |
| 2008/0274904 | A1 | 11/2008 | Gormley et al. |
| 2008/0286762 | A1 | 11/2008 | Miyahara et al. |
| 2008/0286767 | A1 | 11/2008 | Miyahara et al. |
| 2009/0024331 | A1 | 1/2009 | Tomaney et al. |
| 2009/0026082 | A1 | 1/2009 | Rothberg et al. |
| 2009/0053724 | A1 | 2/2009 | Roth et al. |
| 2009/0105959 | A1 | 4/2009 | Braverman et al. |
| 2009/0137404 | A1 | 5/2009 | Drmanac et al. |
| 2009/0176200 | A1 | 7/2009 | Wakita et al. |
| 2009/0221438 | A1 | 9/2009 | Kitzman et al. |
| 2009/0312188 | A1 | 12/2009 | Duer et al. |
| 2010/0029498 | A1 | 2/2010 | Gnirke et al. |
| 2010/0035252 | A1 | 2/2010 | Rothberg et al. |
| 2010/0088255 | A1 | 4/2010 | Mann |
| 2010/0105052 | A1 | 4/2010 | Drmanac et al. |
| 2010/0137143 | A1 | 6/2010 | Rothberg et al. |
| 2010/0160172 | A1 | 6/2010 | Erlich et al. |
| 2010/0173303 | A1 | 7/2010 | Ronaghi et al. |
| 2010/0188073 | A1 | 7/2010 | Rothberg et al. |
| 2010/0192032 | A1 | 7/2010 | Chen et al. |
| 2010/0197507 | A1 | 8/2010 | Rothberg et al. |
| 2010/0199155 | A1 | 8/2010 | Kermani et al. |
| 2010/0209922 | A1 | 8/2010 | Williams et al. |
| 2010/0267043 | A1 | 10/2010 | Braverman et al. |
| 2010/0282617 | A1 | 11/2010 | Rothberg et al. |
| 2010/0300559 | A1 | 12/2010 | Schultz et al. |
| 2010/0300895 | A1 | 12/2010 | Noble et al. |
| 2010/0301398 | A1 | 12/2010 | Rothberg et al. |
| 2010/0304447 | A1 | 12/2010 | Harris |
| 2010/0323348 | A1 | 12/2010 | Hamady et al. |
| 2010/0323350 | A1 | 12/2010 | Gordon et al. |
| 2011/0065604 | A1 | 3/2011 | Sampson et al. |
| 2011/0160078 | A1 | 6/2011 | Fodor et al. |
| 2011/0213563 | A1 | 9/2011 | Chen et al. |
| 2011/0230358 | A1 | 9/2011 | Rava |
| 2011/0246084 | A1 | 10/2011 | Ronaghi et al. |
| 2011/0257889 | A1 | 10/2011 | Klammer et al. |
| 2011/0263463 | A1 | 10/2011 | Rothberg et al. |
| 2011/0275522 | A1 | 11/2011 | Rothberg et al. |
| 2011/0281737 | A1 | 11/2011 | Rothberg et al. |
| 2011/0281741 | A1 | 11/2011 | Rothberg et al. |
| 2011/0294115 | A1 | 12/2011 | Williams et al. |
| 2012/0035062 | A1 | 2/2012 | Schultz et al. |
| 2012/0037961 | A1 | 2/2012 | Rothberg et al. |
| 2012/0040844 | A1 | 2/2012 | Rothberg et al. |
| 2012/0046175 | A1 | 2/2012 | Rodesch et al. |
| 2012/0109598 | A1 | 5/2012 | Davey et al. |
| 2012/0172241 | A1 | 7/2012 | Rearick et al. |
| 2012/0173158 | A1 | 7/2012 | Hubbell |
| 2012/0173159 | A1 | 7/2012 | Davey et al. |
| 2012/0220494 | A1 | 8/2012 | Samuels et al. |
| 2012/0264621 | A1 | 10/2012 | Hubbell et al. |
| 2012/0301926 | A1 | 11/2012 | Chen et al. |
| 2013/0060482 | A1 | 3/2013 | Sikora et al. |
| 2014/0243232 | A1 | 8/2014 | Meredith et al. |
| 2015/0087537 | A1 | 3/2015 | Hubbell |
| 2016/0333402 | A1 | 11/2016 | Koller et al. |
| 2017/0321271 | A1 | 11/2017 | Hubbell |

FOREIGN PATENT DOCUMENTS

| | | |
|---|---|---|
| WO | WO 2001/001015 | 1/2001 |
| WO | WO 2005/040425 | 5/2005 |
| WO | 2006084131 A2 | 8/2006 |
| WO | WO 2008/076406 | 6/2008 |
| WO | WO 2009/158006 | 12/2009 |
| WO | 2010003153 A2 | 1/2010 |
| WO | WO 2010/047804 | 4/2010 |
| WO | 2010051978 A1 | 5/2010 |
| WO | WO 2010/077859 | 7/2010 |
| WO | 2010122506 A2 | 10/2010 |
| WO | WO 2010/117804 | 10/2010 |
| WO | WO 2010/138182 | 12/2010 |
| WO | WO 2012/044847 | 4/2012 |
| WO | 2012/129363 | 9/2012 |
| WO | 2013010062 A2 | 1/2013 |

OTHER PUBLICATIONS

U.S. Appl. No. 13/482,542, Chen et al.
Ahmadian et al., "Pyrosequencing: history, biochemistry and future," *Clin. Chim. Acta*, 363:83-94 (2006).
Aksyonov et al., "Multiplexed DNA sequencing-by-synthesis," *Anal. Biochem.*, 348:127-138 (2006).
Anderson et al., "A System for Multiplexed Direct Electrical Detection of DNA Synthesis," *Sens. Actuators B Chem.*, 129(1):79-86 (2008).
Ashlock et al., "DNA error correcting codes: No crossover," *IEEE Symposium on Computational Intelligence in Bioinformatics and Computational Biology*, 38-45 (2009).
Brockman et al., "Quality scores and SNP detection in sequencing-by-synthesis systems," *Genome Res.*, 18:763-770 (2008).
Berger et al., "Compact, universal DNA microarrays to comprehensively determine transcription-factor binding site specificities," *Nat. Biotechnol.*, 24(11):1429-1435 (2006).
Dawson et al., "Synthesis of proteins by native chemical ligation," *Science*, 266:776-779 (1994).
Droege et al., "The Genome Sequencer FLX™ System—Longer reads, more applications, straight forward bioinformatics and more complete data sets," *J. Biotechnol.*, 136:3-10 (2008).
Eltoukhy et al., "Modeling and Base-Calling for DNA Sequencing-By-Synthesis," *2006 IEEE International Conference on Acoustics, Speech, and Signal Processing*, II:1032-1035 (2006).
Faircloth et al., "Large sets of edit-metric sequence identification tags to facilitate large-scale multiplexing of reads from massively parallel sequencing," *Nature Preceding*, 1-15 (2011).
Fakhrai-Rad et al., "Pyrosequencing™: An Accurate Detection Platform for Single Nucleotide Polymorphisms," *Hum. Mutat.*, 19:479-485 (2002).
Fu et al., "Counting individual DNA molecules by the stochastic attachment of diverse labels," *Proc. Natl. Adac. Sci. U.S.A.*, 108(22):9026-9031 (2011).
Golay, M., "Notes on Digital Coding," *Proc. IRE*, 37(6):657 (1949).
Guarizadeh, B., "Method Development and Applications of Pyrosequencing Technology," Doctoral Dissertation, Royal Institute of Technology, Stockholm, Sweden (2003).
Hamady et al., "Error-correcting barcoded primers for pyrosequencing hundreds of samples in multiplex," *Nat. Methods*, 5(3):235-237 (2008).
Hamming, R.W., "Error Detecting and Error Correcting Codes," *Bell Syst. Tech. J.*, 29(2):147-160(1950) (available at http://www.alcatel-lucent.com/bstj/vol29-1950/articles/bstj29-2-147.pdf).

(56) References Cited

OTHER PUBLICATIONS

Ji et al., "BM-BC: A Bayesian method of base calling for Solexa sequence data," *Department of Biostatistics, The University of Texas M. D. Anderson Cancer Center*, Houston, Texas, U.S.A. (http://odin.mdacc.tmc.edu/~ylji/BMBC/bmbc-ie2.pdf), pp. 1-27 (2010).
Kanemasu, M., "Golay Codes," *MIT Undergraduate Journal of Mathematics*, 1:95-99 (1999) (available at http://www-math.mit.edu/phase2/UJM/vol1/MKANEM~1.PDF).
Krishnan et al., "Barcodes for DNA sequencing with guaranteed error correction capability," *Electron. Lett.*, 47(4):1-2 (2011).
Margulies et al., Supplementary Methods for the article "Genome sequencing in microfabricated high-density picolitre reactors," *Nature*. 437:376-380 (2005), pp. 1-34.
Margulies et al., "Genome sequencing in microfabricated high-density picolitre reactors," *Nature*, 437:376-380 (2005).
Muir, T., "Semisynthesis of proteins by expressed protein ligation," *Ann. Rev. Biochem.*, 72:249-289 (2003).
Muralidharan et al., "Protein ligation: an enabling technology for the biophysical analysis of proteins," *Nat. Methods*, 3:429-438 (2006).
Paulus, H., "Protein splicing and related forms of protein autoprocessing", *Annu Rev Biochem*, 69:447-496 (2000).
Pourmand et al., "Direct electrical detection of DNA synthesis," *Proc. Natl. Adac. Sci. U.S.A.*, 103(17):6466-6470 (2006).
Pourmand et al., "Multiplex Pyrosequencing," *Nucleic Acids Res.*, 30(7)(e31):1-5 (2002).
Ronaghi, "Pyrosequencing Sheds Light on DNA Sequencing," *Genome Res.*, 11:3-11 (2001).
Ronaghi et al., "A Sequencing Method Based on Real-Time Pyrophosphate," *Science*, 281(5375):363-365 (1998).
Shiroguchi et al., "Digital RNA sequencing minimizes sequence-dependent bias and amplification noise with optimized single-molecule barcodes," *Proc. Natl. Adac. Sci. U.S.A.*, 109(4):1347-1352 (2012).
Yan et al., "Yeast Barcoders: a chemogenomic application of a universal donor-strain collection carrying bar-code identifiers," *Nat. Methods*, 5(8):719-725 (2008).
Mamanova, et al., "Target-enrichment strategies for next-generation sequencing", Nature Methods, vol. 7 No. 2, Feb. 2010, 111-118.
Gnirke, et al., "Solution hybrid selection with ultra-long oligonucleotides for massively parallel targeted sequencing", Nature Biotechnology, vol. 27 No. 2, Feb. 2009, 182-189.
Hodges, et al., "Hybrid selection of discrete genomic intervals on custom-designed microarrays for massively parallel sequencing", Nature Protocols, vol. 4 No. 6, 2009, 960-974.
Lee, et al., "Improving the efficiency of genomic loci capture using oligonucleotide arrays for high throughput resequencing", BMC Genomics 2009, 10:646, 12 pages.
Sakata, et al., "DNA Sequencing Based on Intrinsic Molecular Charges", Angewandte Chemie 2006, 118, 2283-2286.
Bashiardes, et al., "Direct genomic selection", Nature Methods, vol. 2 No. 1, Jan. 2005, 63-69.
Purushothaman, et al., "Towards Fast Solid State DNA Sequencing", IEEE ISCAS 2002 Proceedings, IV-169-IV-172.
Forney, et al., "The Nordstrom-Robinson Code is the Binary Image of the Octacode", Feb. 8, 2001, 11 pages.
Sakurai, et al., "Real-Time Monitoring of DNA Polymerase Reactions by a Micro ISFET pH Sensor", Anal. Chem. 1992, 64, 1996-1997.
Hoffman, et al., "Coding Theory: The Essentials", Pure and Applied Mathematics, Dec. 1991.
Lin, et al., "Error Control Coding: Fundamentals and Applications", Prentice Hall, Inc., 1983.
P. Bergveld: "Thirty years of Isfetology: what happened in the past 30 years and what may happen in the next 30 years", Sens. Actuators, vol. 88, 2003, pp. 1-20.
Birren et al.: "Go Analysis: a Laboratory Manual Series", vol. I-IV, 1997-1999.
Breslauer et al, Proceedings National Academy of Science USA, vol. 83, No. 11, 1986, pp. 3746-3750.
Casey; Davidson, Nucleic Acids Research, vol. 4, No. 5, 1977, pp. 1539-1552.
Hawkins, Nucleic Acids Research, vol. 23, No. 15, 1995, pp. 2872-2880.
Hytonen et al., BMC Structural Biology, vol. 7, 2007, pp. 1-20.
Rychlik et al, Nucleic Acids Research, vol. 18, No. 21, 1990, pp. 6409-6412.
Tewhey et al., "Enrichment of sequencing targets from the human genome by solution hybridization," Genome Biology 2009, 10:R116.
Wetmur, Critical Reviews in Biochemistry and Molecular Biology, vol. 26, 1991, pp. 227-259.
Wetmur, J. Mol. Biol., vol. 31, 1968, pp. 349-370.
Tilo Buschmann et al., "Levenshtein error-correcting barcodes for multiplexed Dna sequencing", BMC Bioinformatics, vol. 14, No. 1, Jan. 1, 2013.
Leonid V. Bystrykh et al., "Generalized DNA Barcode Design Based on Hamming Codes", vol. 7, No. 5, May 17, 2012.
Lennon, N. J., A scalable, fully automated process for construction of sequence-ready barcoded libraries for 454. Genome Biology 11, (2010).
Page Pacific Biosciences et al: "PacBio SampleNet—Shared Protocol Guidelines for Using PacBio Barcodes for SMRT", Jan. 1, 2014.
Parameswaran, P. et al., A pyrosequencing-tailored nucleotide barcode design unveils opportunities for large-scale sample multiplexing. Nucleic Acids Research 35, e130:1-9 (2007).
Lehninger, "Biochemistry," Chapter 24: Digestion, Transport, and Integration of Metabolism, pp. 701, 702, and, 707, Worth Publishers (1982).
"PCR Primer: a Laboratory Manual," 2nd, ed., Contents, pp. vii-ix, Cold Spring Harbor Laboratory Press (2003).
International Search Report and Written Opinion for International Application No. PCT/US2016/032442, dated Aug. 5, 2016, 15 pages.
Final Office Action in U.S. Appl. No. 14/505,636, dated Sep. 28, 2015, 16 pages.
International Search Report and Written Opinion for International Application No. PCT/US2012/046624, dated Jan. 4, 2013, 15 pages.
Database Geneseq, "HIV1_8 DNA amplicon flanking adaptor, SEQ ID 371", Database accession No. AYL45091 (Dec. 23, 2010).

| primer site | key | barcode 1 | target sequence 1 |
|---|---|---|---|
| primer site | key | barcode 2 | target sequence 2 |
| primer site | key | barcode 3 | target sequence 3 |
| primer site | key | barcode 4 | target sequence 4 |
| primer site | key | barcode 5 | target sequence 5 |
| primer site | key | barcode 6 | target sequence 6 |
| primer site | key | barcode 7 | target sequence 7 |

FIG. 9

METHODS, SYSTEMS, COMPUTER READABLE MEDIA, AND KITS FOR SAMPLE IDENTIFICATION

CROSS-REFERENCE TO RELATED APPLICATIONS

This application claims the benefit of U.S. Prov. Pat. Appl. No. 61/545,290, filed Oct. 10, 2011, and U.S. Prov. Pat. Appl. No. 61/529,687, filed Aug. 31, 2011, which are both incorporated by reference herein in their entirety.

SEQUENCE LISTING

This application contains a Sequence Listing, which has been submitted in ASCII format via EFS-Web and is hereby incorporated by reference in its entirety. Said ASCII copy is named LT00574_ST25.txt, was created on Nov. 5, 2012, and is 4,144 bytes in size.

FIELD

This application generally relates to methods, systems, computer readable media, and kits for sample identification, and, more specifically, to methods, systems, computer readable media, and kits for designing and/or making and/or using sample discriminating codes or barcodes for identifying sample nucleic acids or other biomolecules or polymers.

BACKGROUND

Various instruments, apparatuses, and/or systems perform sequencing of nucleic acid sequences using sequencing-by-synthesis, including, for example, the Genome Analyzer/HiSeq/MiSeq platforms (Illumina, Inc.; see, e.g., U.S. Pat. Nos. 6,833,246 and 5,750,341); the GS FLX, GS FLX Titanium, and GS Junior platforms (Roche/454 Life Sciences; see, e.g., Ronaghi et al., SCIENCE, 281:363-365 (1998), and Margulies et al., NATURE, 437:376-380 (2005)); and the Ion PGM™ and Ion Proton™ Sequencers (Life Technologies Corp./Ion Torrent; see, e.g., U.S. Pat. No. 7,948,015 and U.S. Pat. Appl. Publ. Nos. 2010/0137143, 2009/0026082, and 2010/0282617, which are all incorporated by reference herein in their entirety). In order to increase sequencing throughput and/or lower costs for sequencing-by-synthesis (and other sequencing methods such as, e.g., sequencing-by-hybridization, sequencing-by-ligation, etc.), there is a need for new methods, systems, computer readable media, and kits that allow highly efficient preparation and/or identification of samples of potentially high complexity.

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

FIG. 9 illustrates a pool of seven different polynucleotide strands, each with a unique barcode sequence.

EXEMPLARY EMBODIMENTS

Figure 1A:
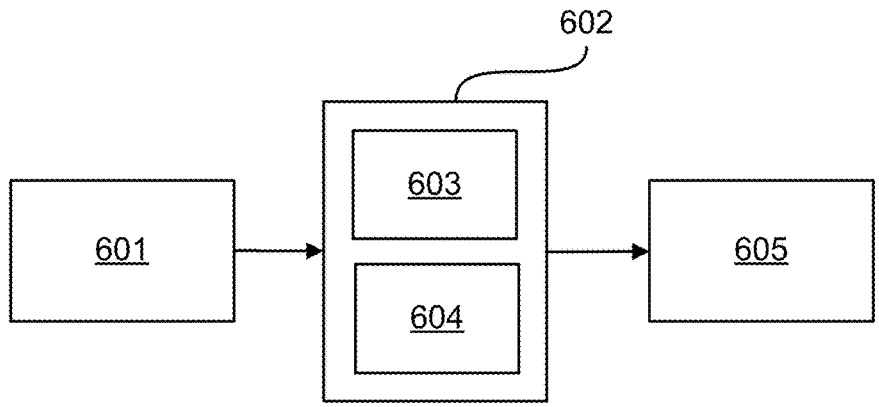
FIG. 1A illustrates an exemplary system for obtaining, processing, and/or analyzing multiplex nucleic acid sequencing data.

The following description and the various embodiments described herein are exemplary and explanatory only and are not to be construed as limiting or restrictive in any way. Other embodiments, features, objects, and advantages of the present teachings will be apparent from the description and accompanying drawings, and from the claims.

In accordance with the teachings and principles embodied in this application, new methods, systems, computer readable media, and kits that allow highly efficient preparation and/or identification of samples of potentially high complexity are provided. The new methods, systems, computer readable media, and kits may help increase throughput by allowing contemporaneous sequencing and/or analysis of multiple samples (e.g., multiplexed sequencing), facilitated by using sample discriminating codes or coded molecular constructs. Multiplexed sequencing may allow multiple coded samples (for example, different samples or samples from different sources) to be analyzed substantially simultaneously in a single sequencing run (e.g., on a common slide, chip, substrate, or other sample holder device).

In accordance with the teachings and principles embodied in this application, new methods, systems, computer readable media, and kits allowing identification of an origin of samples used in multiplexed sequencing are provided. Such identification may involve an analysis of sequencing data for the samples. The source of the sequencing data may be uniquely tagged, coded, or identified (e.g., to resolve a particular nucleic acid species associated with a particular sample population). Such identification may be facilitated by using unique sample discriminating codes or sequences (also known as barcodes, e.g., nucleic acid barcodes) that may be embedded within or otherwise associated with the samples. Such discriminators are not, however, immune to errors or misreads that may occur during sequencing. For example, an erroneous barcode read may alter interpretation of the barcode information, which may render the barcode unrecognizable and prevent correct sample identification. An erroneous barcode read may also result in the association of a sample to an incorrect sample source or population of origin, which may be particularly useful in clinical samples.

In accordance with the teachings and principles embodied in this application, new methods, systems, computer readable media, and kits that may help address the problem of detecting and/or correcting errors that can arise during the sequencing of samples comprising barcodes are provided. In various embodiments, sample discriminating codes or sequences or barcodes and methodologies for developing robust sample discriminating codes or sequences or barcodes that incorporate an error-tolerant code (e.g., an error-correcting code or an error-detecting code) are provided.

Unless otherwise specifically designated herein, terms, techniques, and symbols of biochemistry, cell biology, cell and tissue culture, genetics, molecular biology, nucleic acid chemistry, and organic chemistry (including chemical and physical analysis of polymer particles, enzymatic reactions and purification, nucleic acid purification and preparation, nucleic acid sequencing and analysis, polymerization techniques, preparation of synthetic polynucleotides, recombinant techniques, etc.) used herein follow those of standard treatises and texts in the relevant field. See, e.g., Kornberg and Baker, DNA REPLICATION, 2nd ed. (W.H. Freeman, New York, 1992); Lehninger, BIOCHEMISTRY, 2nd ed. (Worth Publishers, New York, 1975); Strachan and Read, HUMAN MOLECULAR GENETICS, 2nd ed. (Wiley-Liss, New York, 1999); Birren et al. (eds.), GENOME ANALYSIS: A LABORATORY MANUAL SERIES (Vols. I-IV), Dieffenbach and Dveksler (eds.), PCR PRIMER: A LABORATORY MANUAL, and Green and Sambrook (eds.), MOLECULAR CLONING: A LABORATORY MANUAL (all from Cold Spring Harbor Laboratory Press); and Hermanson, BIOCONJUGATE TECHNIQUES, 2nd ed. (Academic Press, 2008).

As used herein, "amplifying" generally refers to performing an amplification reaction. As used herein, "amplicon" generally refers to a product of a polynucleotide amplification reaction, which includes a clonal population of polynucleotides, which may be single stranded or double stranded and which may be replicated from one or more starting sequences. The one or more starting sequences may be one or more copies of the same sequence, or they may be a mixture of different sequences that contain a common region that is amplified such as, for example, a specific exon sequence present in a mixture of DNA fragments extracted from a sample. Preferably, amplicons may be formed by the amplification of a single starting sequence. Amplicons may be produced by a variety of amplification reactions whose products comprise replicates of one or more starting, or target, nucleic acids. Amplification reactions producing amplicons may be "template-driven" in that base pairing of reactants, either nucleotides or oligonucleotides, have complements in a template polynucleotide that are required for the creation of reaction products. Template-driven reactions may be primer extensions with a nucleic acid polymerase or oligonucleotide ligations with a nucleic acid ligase. Such reactions include, for example, polymerase chain reactions (PCRs), linear polymerase reactions, nucleic acid sequence-based amplifications (NASBAs), rolling circle amplifications, for example, or using rolling circle amplification to form a single body that may exclusively occupy a microwell as disclosed in Drmanac et al., U.S. Pat. Appl. Publ. No. 2009/0137404, which is incorporated by reference herein in its entirety. As used herein, "solid phase amplicon" generally refers to a solid phase support, such as a particle or bead, to which is attached a clonal population of nucleic acid sequences, which may have been produced by a emulsion PCR, for example.

As used herein, "analyte" generally refers to a molecule or biological sample that can directly affect an electronic sensor in a region (such as a defined space or reaction confinement region or microwell, for example) or that can indirectly affect such an electronic sensor by a by-product from a reaction involving such molecule or biological cell located in such region. In an embodiment, an analyte may be a sample or template nucleic acid, which may be subjected to a sequencing reaction, which may, in turn, generate a reaction by-product, such as one or more hydrogen ions, that can affect an electronic sensor. The term "analyte" also comprehends multiple copies of analytes, such as proteins, peptides, nucleic acids, for example, attached to solid supports, such as beads or particles, for example. In an embodiment, an analyte may be a nucleic acid amplicon or a solid phase amplicon. A sample nucleic acid template may be associated with a surface via covalent bonding or a specific binding or coupling reaction, and may be derived from, for example, a shot-gun fragmented DNA or amplicon library (which are examples of library fragments further discussed herein), or a sample emulsion PCR process creating clonally-amplified sample nucleic acid templates on particles such as IonSphere™ particles. An analyte may include particles having attached thereto clonal populations of DNA fragments, e.g., genomic DNA fragments, cDNA fragments, for example.

As used herein, "primer" generally refers to an oligonucleotide, either natural or synthetic, that is capable, upon forming a duplex with a polynucleotide template, of acting as a point of initiation of nucleic acid synthesis and being extended from its 3' end along the template so that an extended duplex may be formed. Extension of a primer may be carried out with a nucleic acid polymerase, such as a DNA or RNA polymerase. The sequence of nucleotides added in the extension process may be determined by the sequence of the template polynucleotide. Primers may have a length in the range of from 14 to 40 nucleotides, or in the range of from 18 to 36 nucleotides, for example, or from N to M nucleotides where N is an integer larger than 18 and M is an integer larger than N and smaller than 36, for example. Other lengths are of course possible. Primers may be employed in a variety of amplification reactions, including linear amplification reactions using a single primer, or polymerase chain reactions, employing two or more primers, for example. Guidance for selecting the lengths and sequences of primers may be found in Dieffenbach and Dveksler (eds.), PCR PRIMER: A LABORATORY MANUAL, 2nd ed. (Cold Spring Harbor Laboratory Press, New York, 2003).

As used herein, "polynucleotide" or "oligonucleotide" generally refers to a linear polymer of nucleotide monomers and may be DNA or RNA. Monomers making up polynucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, for example. Such monomers and their internucleosidic linkages may be naturally occurring or may be analogs thereof, e.g., naturally occurring or non-naturally occurring analogs. Non-naturally occurring analogs may include PNAs, phosphorothioate internucleosidic linkages, bases containing linking groups permitting the attachment of labels, such as fluorophores, or haptens, for example. In an embodiment, oligonucleotide may refer to smaller polynucleotides, for example, having 5-40 monomeric units. Polynucleotides may include the natural deoxyribonucleosides (e.g., deoxyadenosine, deoxycytidine, deoxyguanosine, and deoxythymidine for DNA or their ribose counterparts for RNA) linked by phosphodiester linkages. However, they may also include non-natural nucleotide analogs, e.g., including modified bases, sugars, or internucleosidic linkages. In an embodiment, a polynucleotide may be represented by a sequence of letters (upper or lower case), such as "ATGCCTG," and it will be understood that the nucleotides are in 5'→3' order from left to right and that "A" denotes deoxyadenosine, "C" denotes deoxycytidine, "G" denotes deoxyguanosine, and "T" denotes deoxythymidine, and that "I" denotes deoxyinosine, and "U" denotes deoxyuridine, unless otherwise indicated or obvious from context. Whenever the use of an oligonucleotide or polynucleotide requires enzymatic processing, such as extension by a polymerase, ligation by a ligase, oligonucleotides or polynucleotides in those instances may not contain certain analogs of internucleosidic linkages, sugar moieties, or bases at any or some positions. Unless otherwise noted the terminology and atom numbering conventions will follow those disclosed in Strachan and Read, HUMAN MOLECULAR GENETICS, 2nd ed. (Wiley-Liss, New York, 1999). Polynucleotides may range in size from a few monomeric units, e.g., 5-40, to several thousand monomeric units, for example.

As used herein, "defined space" (or "reaction space," which may be used interchangeably with "defined space") generally refers to any space or region (which may be in one, two, or three dimensions) in which at least some of a molecule, fluid, and/or solid can be confined, retained and/or localized. The space may be a predetermined area (which may be a flat area) or volume, and may be defined, for example, by a depression or a micro-machined well in or associated with a microwell plate, microtiter plate, microplate, or a chip. The area or volume may also be determined based on an amount of fluid or solid, for example, deposited on an area or in a volume otherwise defining a space. For example, isolated hydrophobic areas on a generally hydrophobic surface may provide defined spaces. In an embodiment, a defined space may be a reaction chamber, such as a well or a microwell, which may be in a chip. In an embodiment, a defined space may be a substantially flat area on a substrate without wells, for example. A defined space may contain or be exposed to enzymes and reagents used in nucleotide incorporation.

As used herein, "reaction confinement region" generally refers to any region in which a reaction may be confined and includes, for example, a "reaction chamber," a "well," and a "microwell" (each of which may be used interchangeably). A reaction confinement region may include a region in which a physical or chemical attribute of a solid substrate can permit the localization of a reaction of interest, and a discrete region of a surface of a substrate that can specifically bind an analyte of interest (such as a discrete region with oligonucleotides or antibodies covalently linked to such surface), for example. Reaction confinement regions may be hollow or have well-defined shapes and volumes, which may be manufactured into a substrate. These latter types of reaction confinement regions are referred to herein as microwells or reaction chambers, may be fabricated using any suitable microfabrication techniques, and may have volume, shape, aspect ratio (e.g., base width-to-well depth ratio), and other dimensional characteristics that may be selected depending on particular applications, including the nature of reactions taking place as well as the reagents, by-products, and labeling techniques (if any) that are employed. Reaction confinement regions may also be substantially flat areas on a substrate without wells, for example. In various embodiments, microwells may be fabricated using any suitable fabrication technique known in the art. Exemplary configurations (e.g., spacing, shape, and volume) of microwells or reaction chambers are disclosed in Rothberg et al., U.S. Pat. Publ. Nos. 2009/0127589 and 2009/0026082; Rothberg et al., U.K. Pat. Appl. Publ. No. GB 2461127; and Kim et al., U.S. Pat. No. 7,785,862, which are all incorporated by reference in their entirety.

Defined spaces or reaction confinement regions may be arranged as an array, which may be a substantially planar one-dimensional or two-dimensional arrangement of elements such as sensors or wells. The number of columns (or rows) of a two-dimensional array may or may not be the same. Preferably, the array comprises at least 100,000 chambers. Preferably, each reaction chamber has a horizontal width and a vertical depth that has an aspect ratio of about 1:1 or less. Preferably, the pitch between the reaction chambers is no more than about 10 microns. Preferably, each reaction chamber is no greater than 10 $\mu m^3$ (i.e., 1 pL) in volume, or no greater than 0.34 pL in volume, and more preferably no greater than 0.096 pL or even 0.012 pL in volume. A reaction chamber may be $2^2$, $3^2$, $4^2$, $5^2$, $6^2$, $7^2$, $8^2$, $9^2$, or $10^2$ square microns in cross-sectional area at the top, for example. Preferably, the array may have at least $10^2$, $10^3$, $10^4$, $10^5$, $10^6$, $10^7$, $10^8$, $10^9$, or more reaction chambers, for example. The reaction chambers may be capacitively coupled to chemFETs.

Defined spaces or reaction confinement regions, whether arranged as an array or in some other configuration, may be in electrical communication with at least one sensor to allow detection or measurement of one or more detectable or measurable parameter or characteristics. The sensors may convert changes in the presence, concentration, or amounts of reaction by-products (or changes in ionic character of reactants) into an output signal, which may be registered electronically, for example, as a change in a voltage level or a current level which, in turn, may be processed to extract information about a chemical reaction or desired association event, for example, a nucleotide incorporation event. The sensors may include at least one chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of a physical property (or a change in such value), such as an ion concentration. An initial measurement or interrogation of a pH for a defined space or reaction confinement region, for example, may be represented as an electrical signal or a voltage, which may be digitalized (e.g., converted to a digital representation of the electrical signal or the voltage). Any of these measurements and representations may be considered raw data or a raw signal.

As used herein, "nucleic acid template" (or "sequencing template," which may be used interchangeably with "nucleic acid template") generally refers to a nucleic acid sequence that is a target of one or more nucleic acid sequencing reactions. A sequence for a nucleic acid template may comprise a naturally-occurring or synthetic nucleic acid sequence. A sequence for a nucleic acid template may also include a known or unknown nucleic acid sequence from a sample of interest. In various embodiments, a nucleic acid template may be attached to a solid support such as, e.g., a bead, microparticle, flow cell, or any other surface, support, or object.

As used herein, "fragment library" generally refers to a collection of nucleic acid fragments in which one or more fragments are used as a sequencing template. A fragment library may be generated in numerous ways (e.g., by cutting, shearing, restricting, or otherwise subdividing a larger nucleic acid into smaller fragments). Fragment libraries may be generated or obtained from naturally occurring nucleic acids, such as, for example, from bacteria, cancer cells, normal cells, or solid tissue. Libraries comprising synthetic nucleic acid sequences may also be generated to create a synthetic fragment library.

As used herein, "mate pair library" generally refers to a collection of nucleic acid sequences comprising two or more fragments having a particular relationship, such as being separated by a known number of nucleotides, for example. Mate pair fragments may be generated in numerous ways (e.g., by cutting, shearing, restricting, or otherwise subdividing a larger nucleic acid and associating the sequence fragments from the ends of the resulting fragments or by associating other subsequences of the resulting fragments). Mate pair libraries may be generated, for example, by circularizing a nucleic acid with an internal adapter construct and then removing the middle portion of the nucleic acid to create a linear strand of nucleic acid comprising the internal adapter with the sequences from the ends of the nucleic acid attached to either end of the internal adapter. Like fragment libraries, mate pair libraries may be generated or obtained from naturally occurring nucleic acid sequences, such as, for example, from bacteria, cancer cells, normal cells, or solid tissue. Synthetic mate pair libraries may also be generated, e.g., by attaching synthetic nucleic acid sequences to either end of an internal adapter sequence.

As used herein, a "molecular sample discriminating code" (or "molecular barcode," which may be used interchangeably with "molecular sample discriminating code") generally refers to an identifiable or resolvable molecular marker, which may be uniquely resolved and may be attached to a sample nucleic acid, biomolecule, or polymer, for example. Such a molecular sample discriminating code may be used for tracking, sorting, separating, and/or identifying sample nucleic acids, biomolecules, or polymers, and may be designed to have properties useful for manipulating nucleic acids, biomolecules, polymers, or other molecules. Molecular sample discriminating codes may comprise the same kind or type of material or subunits comprising the nucleic acid, biomolecule, or polymer they are intended to identify, or they may comprise one or more different material(s) or subunit(s). A molecular sample discriminating code may comprise a short nucleic acid comprising a known or predetermined sequence. A molecular sample discriminating code may be a nucleic acid sample discriminating code (or nucleic acid barcode), which may be an identifiable or resolvable nucleotide sequence (e.g., an oligonucleotide or polynucleotide sequence), and which may include one or more restriction endonuclease recognition sequences or cleavage sites, overhang ends, adaptor sequences, primer sequences, and the like (including combinations of features or properties). A molecular sample discriminating code may be a biopolymer sample discriminating code, which may include one or more antibody recognition sites, restriction sites, intra- or inert-molecule binding sites, and the like (including combinations of features or properties). A plurality of different molecular sample discriminating codes may be used to identify or characterize samples belonging to a common group, and may be attached to, coupled with, or otherwise associated with libraries of nucleic acids, biomolecules, polymers, or other molecules, for example. A molecular sample discriminating code or molecular barcode may be represented by a sample discriminating code or sequence or barcode, which may comprise a set of symbols, components, or characters that may be used to represent or define a molecular sample discriminating code or barcode. For example, a sample discriminating code or barcode may comprise a sequence of letters defining a known or predetermined sequence of nucleic acid bases or other biomolecule or polymer constituents. Sample discriminating codes or barcodes may be used in a variety of sets, subsets, and groupings. Sample discriminating codes or barcodes may be read, or otherwise recognized, identified, or interpreted as a function of a sequence or other arrangement or relationship of subunits that together form a code. Sample discriminating codes or barcodes may also contain one or more additional functional elements including key sequences for quality control and sample detection, primer sites, adaptors for ligation, linkers for attaching to substrates, inserts, etc., for example.

FIG. 1A illustrates an exemplary system for obtaining, processing, and/or analyzing multiplex nucleic acid sequencing data. The system includes a sequencing instrument 601, a server 602 or other computing means or resource, and one or more end user computers 605 or other computing means or resource. The sequencing instrument 601 may be configured to process samples comprising barcodes and to deliver reagents according to a predetermined ordering. The predetermined ordering may be based on a cyclical, repeating pattern of consecutive repeats of a predetermined reagent flow ordering (e.g., consecutive repeats of predetermined sequence of four nucleotide reagents such as "TACG TACG . . . "), or may be based on a random reagent flow ordering, or may be based on an ordering comprising in whole or in part a phase-protecting reagent flow ordering as described in Hubbell et al., U.S. patent application Ser. No. 13/440,849, filed Apr. 5, 2012, which is incorporated by reference herein in its entirety, or some combination thereof. The server 602 may include a processor 603 and a memory and/or database 604. The sequencing instrument 601 and the server 602 may include one or more computer readable media for obtaining, processing, and/or analyzing multiplex nucleic acid sequencing data. In an embodiment, the barcodes may be determined at least in part as a function of the ordering. In an embodiment, the barcodes may comprises codewords of an error-tolerant code, which codewords may be represented in flowspace rather than base space (e.g., may comprise digits or characters corresponding to numbers of nucleotide incorporations responsive to predetermined nucleotide flows rather than actual bases such as nucleic acid bases in base space). In an embodiment, the instrument and the server or other computing means or resource may be configured as a single component. One or more of these components may be used to perform or implement one or more aspects of the embodiments described herein.

Figure 1B:
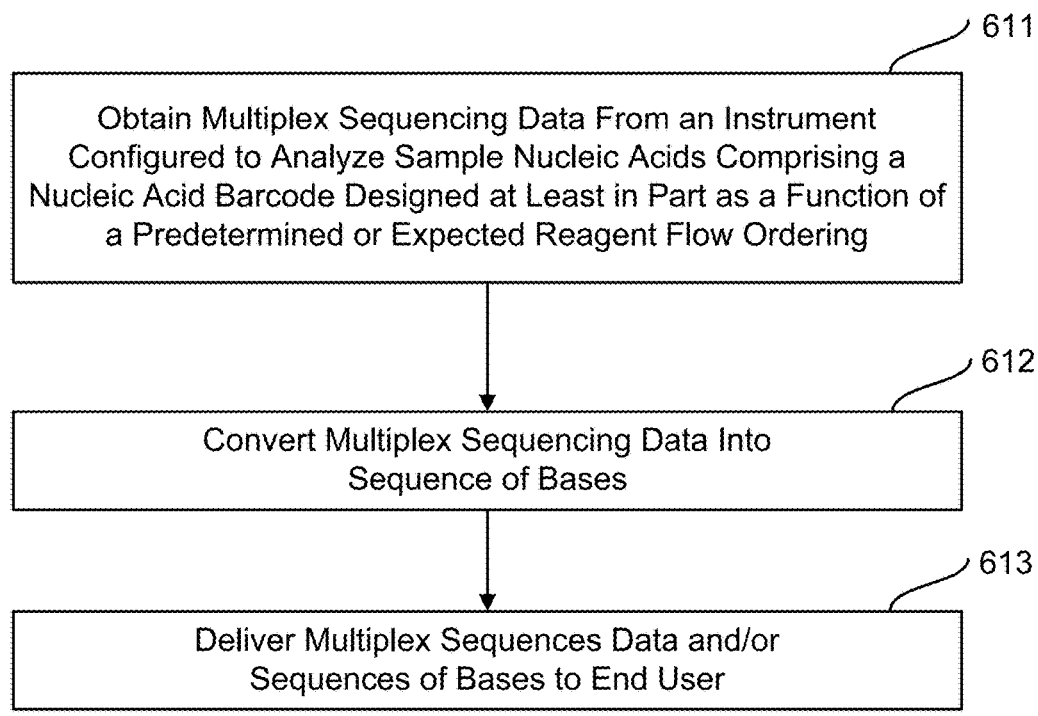
FIG. 1B illustrates an exemplary method for obtaining, processing, and/or analyzing multiplex nucleic acid sequencing data.

FIG. 1B illustrates an exemplary method for obtaining, processing, and/or analyzing multiplex nucleic acid sequencing data. In step 611, a user obtains multiplex sequencing data from an instrument configured to analyze sample nucleic acids comprising a nucleic acid barcode designed at least in part as a function of a predetermined or expected reagent flow ordering. The multiplex sequencing data may include signal data indicative of hydrogen ion concentrations, for example. The predetermined ordering may be based on a cyclical, repeating pattern of consecutive repeats of a predetermined reagent flow ordering (e.g., consecutive repeats of predetermined sequence of four nucleotide reagents such as "TACG TACG . . . "), or may be based on a random reagent flow ordering, or may be based on an ordering comprising in whole or in part a phase-protecting reagent flow ordering as described in Hubbell et al., U.S. patent application Ser. No. 13/440,849, filed Apr. 5, 2012, which is incorporated by reference herein in its entirety, or some combination thereof. In step 612, a server or other computing means or resource converts the multiplex sequencing data into sequences of bases. In step 613, the server or other computing means or resource delivers the multiplex sequencing data and/or sequences of bases to an end user. One or more of these steps and/or components may be used to perform or implement one or more aspects of the embodiments described herein.

In various embodiments, the methods, systems, computer readable media, and kits described herein may advantageously be used to determine the sequence and/or identity of one or more nucleic acid samples using sequencing-by-synthesis. In sequencing-by-synthesis, the sequence of a target nucleic acid may be determined by the stepwise synthesis of complementary nucleic acid strands on a target nucleic acid (whose sequence and/or identity is to be determined) serving as a template for the synthesis reactions (e.g., by a polymerase extension reaction that typically includes the formation of a complex comprising a template (or target polynucleotide), a primer annealed thereto, and a polymerase operably coupled or associated with the primer-template hybrid so as to be capable of incorporating a nucleotide species (e.g., a nucleoside triphosphate, a nucleotide triphosphate, a precursor nucleoside or nucleotide) to the primer). During sequencing-by-synthesis, nucleotides may be sequentially added to growing polynucleotide molecules or strands at positions complementary to template polynucleotide molecules or strands. The addition of the nucleotides to the growing complementary strands, which may be detected using a variety of methods (e.g., pyrosequencing, fluorescence detection, and label-free electronic detection), may be used to identify the sequence composition of the template nucleic acid. This process may be iterated until a complete or selected sequence length complementary to the template has been synthesized.

In various embodiments, the methods, systems, computer readable media, and kits described herein may advantageously be used to generate, process, and/or analyze data and signals obtained using electronic or charged-based nucleic acid sequencing. In electronic or charged-based sequencing (such as, e.g., pH-based sequencing), a nucleotide incorporation event may be determined by detecting ions (e.g., hydrogen ions) generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of deoxynucleoside triphosphate ("dNTP") addition (which may be referred to herein as "nucleotide flows" from which nucleotide incorporations may result) and washing.

The primer may be annealed to the sample or template so that the primer's 3' end can be extended by a polymerase whenever dNTPs complementary to the next base in the template are added. Based on the known sequence of flows and on measured signals indicative of ion concentration during each nucleotide flow, the identity of the type, sequence and number of nucleotide(s) associated with a sample nucleic acid present in a reaction chamber can be determined.

Figure 2A:
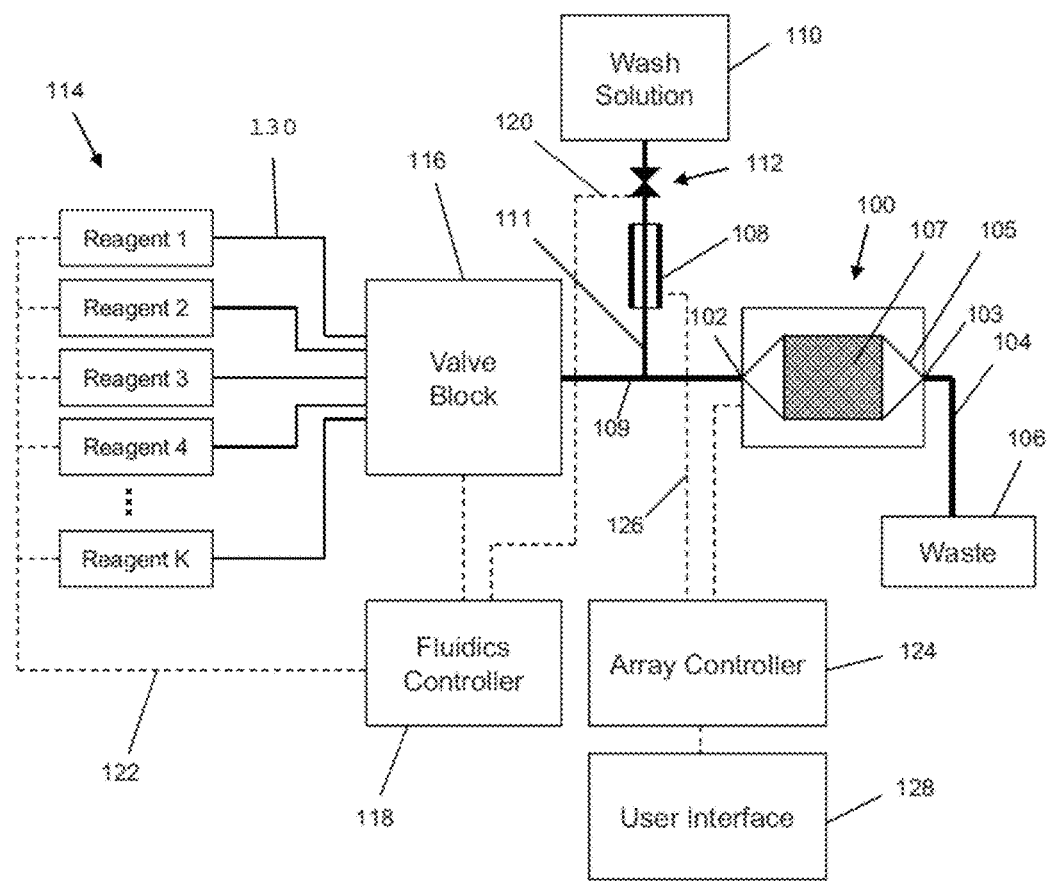
FIG. 2A illustrates components of an exemplary system for nucleic acid sequencing.

FIG. 2A illustrates components of an exemplary system for nucleic acid sequencing. The components include a flow cell and sensor array 100, a reference electrode 108, a plurality of reagents 114, a valve block 116, a wash solution 110, a valve 112, a fluidics controller 118, lines 120/122/126, passages 104/109/111, a waste container 106, an array controller 124, and a user interface 128. The flow cell and sensor array 100 includes an inlet 102, an outlet 103, a microwell array 107, and a flow chamber 105 defining a flow path of reagents over the microwell array 107. The reference electrode 108 may be of any suitable type or shape, including a concentric cylinder with a fluid passage or a wire inserted into a lumen of passage 111. The reagents 114 may be driven through the fluid pathways, valves, and flow cell by pumps, gas pressure, or other suitable methods, and may be discarded into the waste container 106 after exiting the flow cell and sensor array 100. The reagents 114 may, for example, contain dNTPs to be flowed through passages 130 and through the valve block 116, which may control the flow of the reagents 114 to flow chamber 105 (also referred to herein as a reaction chamber) via passage 109. The system may include a reservoir 110 for containing a wash solution that may be used to wash away dNTPs, for example, that may have previously been flowed. The microwell array 107 may include an array of defined spaces or reaction confinement regions, such as microwells, for example, that is operationally associated with a sensor array so that, for example, each microwell has a sensor suitable for detecting an analyte or reaction property of interest. The microwell array 107 may preferably be integrated with the sensor array as a single device or chip. The flow cell may have a variety of designs for controlling the path and flow rate of reagents over the microwell array 107, and may be a microfluidics device. The array controller 124 may provide bias voltages and timing and control signals to the sensor, and collect and/or process output signals. The user interface 128 may display information from the flow cell and sensor array 100 as well as instrument settings and controls, and allow a user to enter or set instrument settings and controls. The system may be configured to let a single fluid or reagent contact the reference electrode 108 throughout an entire multi-step reaction. The valve 112 may be shut to prevent any wash solution 110 from flowing into passage 109 as the reagents are flowing. Although the flow of wash solution may be stopped, there may still be uninterrupted fluid and electrical communication between the reference electrode 108, passage 109, and the sensor array 107. The distance between the reference electrode 108 and the junction between passages 109 and 111 may be selected so that little or no amount of the reagents flowing in passage 109 and possibly diffusing into passage 111 reach the reference electrode 108. In an embodiment, the wash solution 110 may be selected as being in continuous contact with the reference electrode 108, which may be especially useful for multi-step reactions using frequent wash steps. In various embodiments, the fluidics controller 118 may be programmed to control driving forces for flowing reagents 114 and the operation of valve 112 and valve block 116 with any suitable instrument control software, such as LabView (National Instruments, Austin, Tex.), to deliver reagents to the flow cell and sensor array 100 according to a predetermined reagent flow ordering. The reagents may be delivered for predetermined durations, at predetermined flow rates, and may measure physical and/or chemical parameters providing information about the status of one or more reactions taking place in defined spaces or reaction confinement regions, such as, for example, microwells.

Figure 2B:
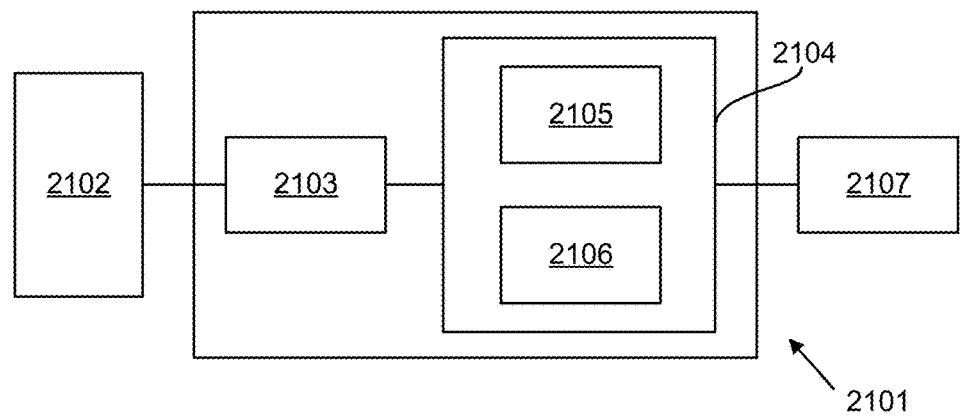
FIG. 2B illustrates an exemplary system for nucleic acid sequencing.

FIG. 2B illustrates an exemplary system 2101 for nucleic acid sequencing. The system includes a reactor array 2102; a reader board 2103; a computer and/or server 2104, which includes a CPU 2105 and a memory 2106; and a display 2107, which may be internal and/or external. One or more of these components may be used to perform or implement one or more aspects of the exemplary embodiments described herein.

Figure 3A:
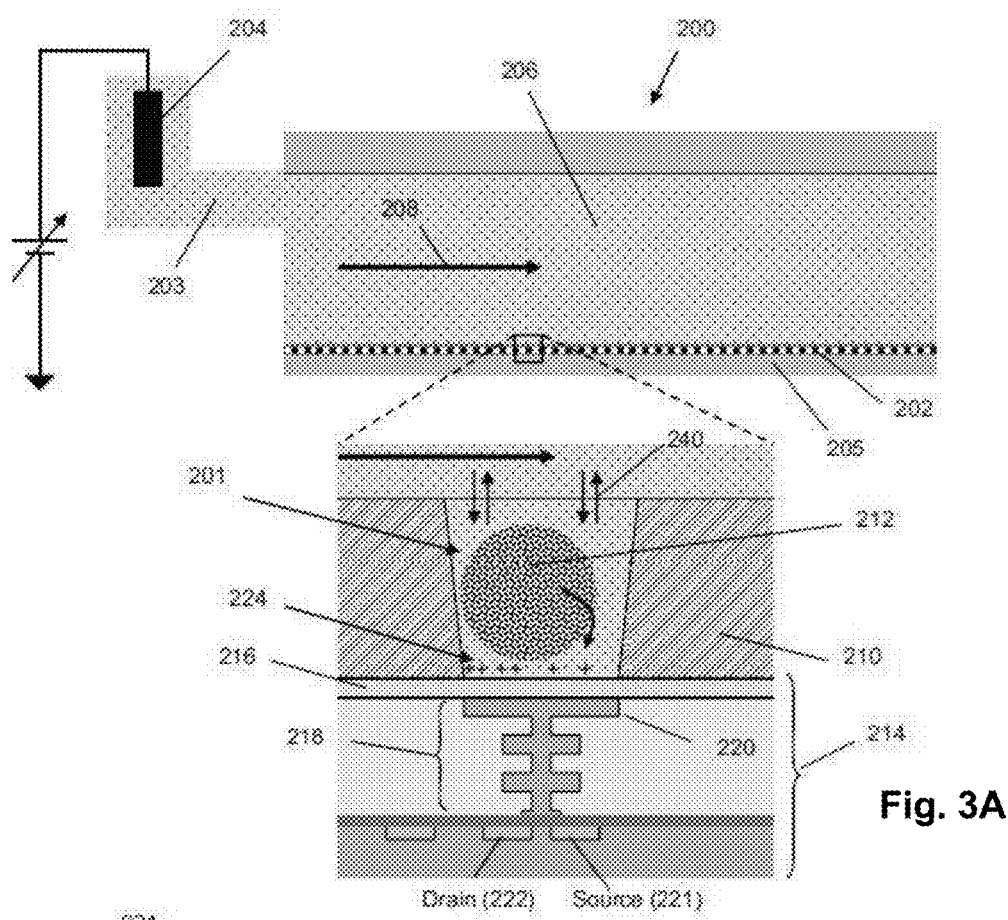
FIG. 3A illustrates cross-sectional and expanded views of an exemplary flow cell for nucleic acid sequencing.

FIG. 3A illustrates cross-sectional and expanded views of an exemplary flow cell 200 for nucleic acid sequencing. The flow cell 200 includes a microwell array 202, a sensor array 205, and a flow chamber 206 in which a reagent flow 208 may move across a surface of the microwell array 202, over open ends of microwells in the microwell array 202. The flow of reagents (e.g., nucleotide species) can be provided in any suitable manner, including delivery by pipettes, or through tubes or passages connected to a flow chamber. The duration, concentration, and/or other flow parameters may be the same or different for each reagent flow. Likewise, the duration, composition, and/or concentration for each wash flow may be the same or different. A microwell 201 in the microwell array 202 may have any suitable volume, shape, and aspect ratio, which may be selected depending on one or more of any reagents, by-products, and labeling techniques used, and the microwell 201 may be formed in layer 210, for example, using any suitable microfabrication technique. A sensor 214 in the sensor array 205 may be an ion sensitive (ISFET) or a chemical sensitive (chemFET) sensor with a floating gate 218 having a sensor plate 220 separated from the microwell interior by a passivation layer 216, and may be predominantly responsive to (and generate an output signal related to) an amount of charge 224 present on the passivation layer 216 opposite of the sensor plate 220. Changes in the amount of charge 224 cause changes in the current between a source 221 and a drain 222 of the sensor 214, which may be used directly to provide a current-based output signal or indirectly with additional circuitry to provide a voltage output signal. Reactants, wash solutions, and other reagents may move into microwells primarily by diffusion 240. One or more analytical reactions to identify or determine characteristics or properties of an analyte of interest may be carried out in one or more microwells of the microwell array 202. Such reactions may generate directly or indirectly by-products that affect the amount of charge 224 adjacent to the sensor plate 220. In an embodiment, a reference electrode 204 may be fluidly connected to the flow chamber 206 via a flow passage 203. In an embodiment, the microwell array 202 and the sensor array 205 may together form an integrated unit forming a bottom wall or floor of the flow cell 200. In an embodiment, one or more copies of an analyte may be attached to a solid phase support 212, which may include microparticles, nanoparticles, beads, gels, and may be solid and porous, for example. The analyte may include a nucleic acid analyte, including a single copy and multiple copies, and may be made, for example, by rolling circle amplification (RCA), exponential RCA, or other suitable techniques to produce an amplicon without the need of a solid support.

Figure 3B:
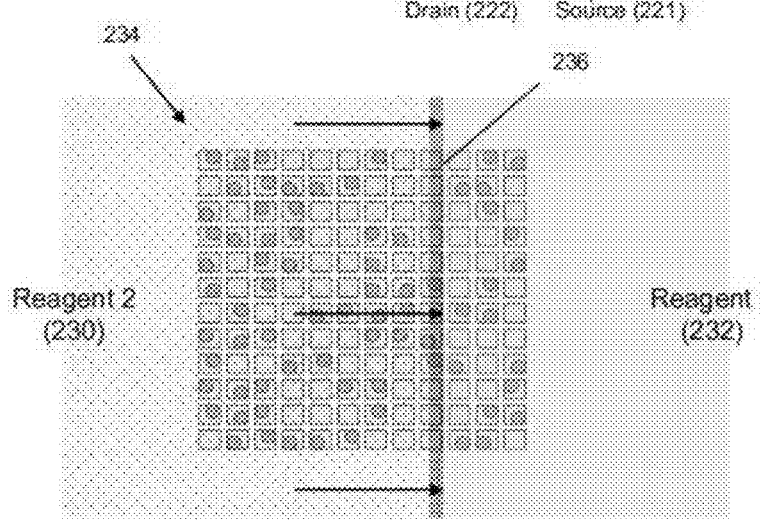
FIG. 3B illustrates an exemplary uniform flow front between successive reagents moving across a section of an exemplary microwell array.

FIG. 3B illustrates an exemplary uniform flow front between successive reagents moving across a section 234 of an exemplary microwell array. A "uniform flow front" between first reagent 232 and second reagent 230 generally refers to the reagents undergoing little or no mixing as they move, thereby keeping a boundary 236 between them narrow. The boundary may be linear for flow cells having inlets and outlets at opposite ends of their flow chambers, or it may be curvilinear for flow cells having central inlets (or outlets) and peripheral outlets (or inlets). In an embodiment, the flow cell design and reagent flow rate may be selected so that each new reagent flow with a uniform flow front as it transits the flow chamber during a switch from one reagent to another.

Figure 4:
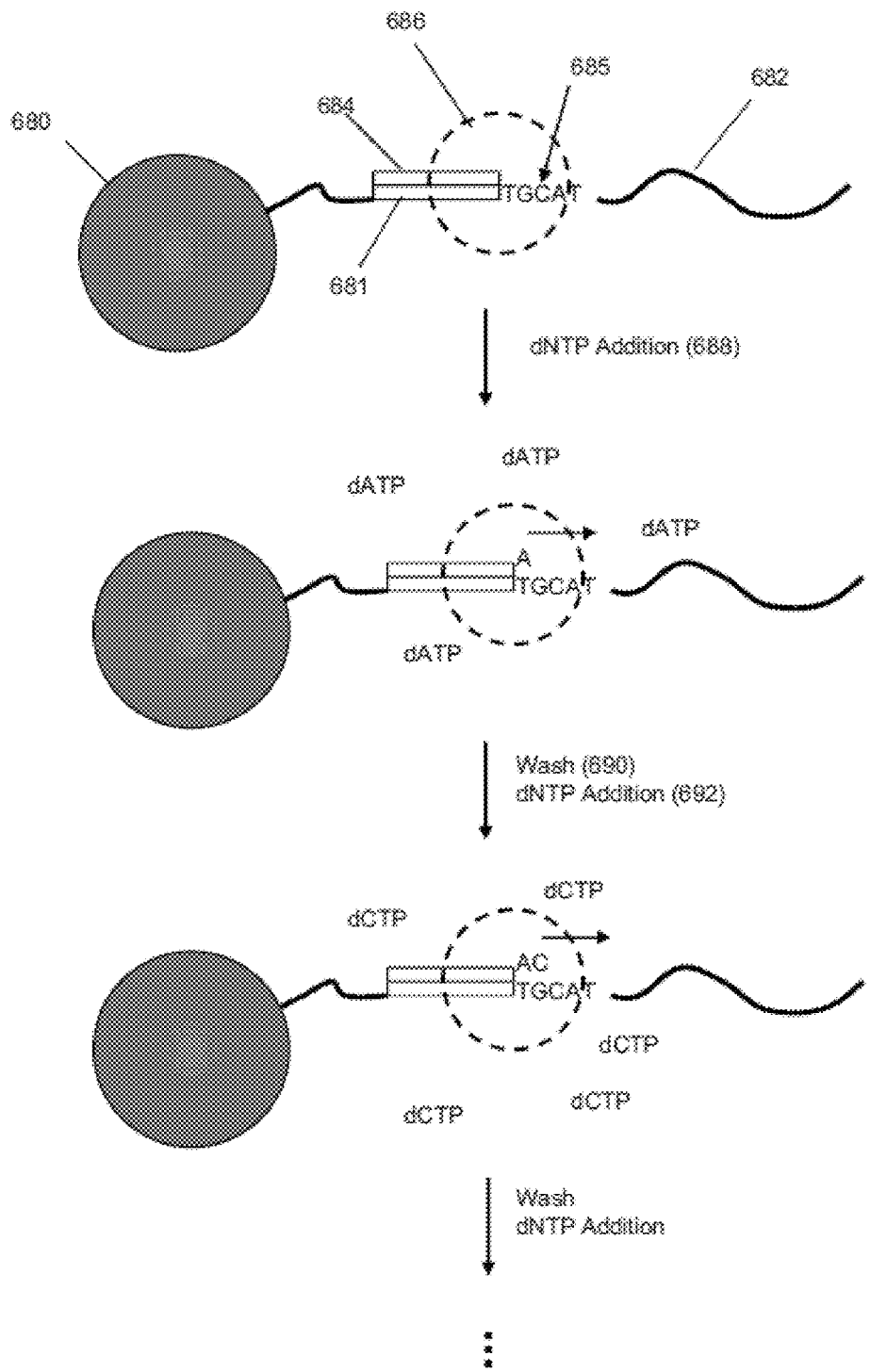
FIG. 4 illustrates an exemplary process for label-free, pH-based sequencing.

FIG. 4 illustrates an exemplary process for label-free, pH-based sequencing. A template 682 with sequence 685 and a primer binding site 681 are attached to a solid phase support 680. The template 682 may be attached as a clonal population to a solid support, such as a microparticle or bead, for example, and may be prepared as disclosed in Leamon et al., U.S. Pat. No. 7,323,305, which is incorporated by reference herein in its entirety. In an embodiment, the template may be associated with a substrate surface or present in a liquid phase with or without being coupled to a support. A primer 684 and DNA polymerase 686 are operably bound to the template 682. As used herein, "operably bound" generally refers to a primer being annealed to a template so that the primer's 3' end may be extended by a polymerase and that a polymerase is bound to such primer-template duplex (or in close proximity thereof) so that binding and/or extension may take place when dNTPs are added. In step 688, dNTP (shown as dATP) is added, and the DNA polymerase 686 incorporates a nucleotide "A" (since "T" is the next nucleotide in the template 682 and is complementary to the flowed dATP nucleotide). In step 690, a wash is performed. In step 692, the next dNTP (shown as dCTP) is added, and the DNA polymerase 686 incorporates a nucleotide "C" (since "G" is the next nucleotide in the template 682). The pH-based nucleic acid sequencing, in which base incorporations may be determined by measuring hydrogen ions that are generated as natural by-products of polymerase-catalyzed extension reactions, may be performed using at least in part one or more features of Anderson et al., A SYSTEM FOR MULTIPLEXED DIRECT ELECTRICAL DETECTION OF DNA SYNTHESIS, Sensors and Actuators B: Chem., 129:79-86 (2008); Rothberg et al., U.S. Pat. Appl. Publ. No. 2009/0026082; and Pourmand et al., DIRECT ELECTRICAL DETECTION OF DNA SYNTHESIS, Proc. Natl. Acad. Sci., 103:6466-6470 (2006), which are all incorporated by reference herein in their entirety. In an embodiment, after each addition of a dNTP, an additional step may be performed in which the reaction chambers are treated with a dNTP-destroying agent, such as apyrase, to eliminate any residual dNTPs remaining in the chamber that might result in spurious extensions in subsequent cycles.

In an embodiment, the primer-template-polymerase complex may be subjected to a series of exposures of different nucleotides in a predetermined or known sequence or ordering. If one or more nucleotides are incorporated, then the signal resulting from the incorporation reaction may be detected, and after repeated cycles of nucleotide addition, primer extension, and signal acquisition, the nucleotide sequence of the template strand may be determined. The output signals measured throughout this process depend on the number of nucleotide incorporations. Specifically, in each addition step, the polymerase extends the primer by incorporating added dNTP only if the next base in the template is complementary to the added dNTP. If there is one complementary base, there is one incorporation; if two, there are two incorporations; if three, there are three incorporations, and so on. With each incorporation, an hydrogen ion is released, and collectively a population released hydrogen ions change the local pH of the reaction chamber. The production of hydrogen ions may be monotonically related to the number of contiguous complementary bases in the template (as well as to the total number of template molecules with primer and polymerase that participate in an extension reaction). Thus, when there is a number of contiguous identical complementary bases in the template (which may represent a homopolymer region), the number of hydrogen ions generated and thus the magnitude of the local pH change is proportional to the number of contiguous identical complementary bases (and the corresponding output signals are then sometimes referred to as "1-mer," "2-mer," "3-mer" output signals, etc.). If the next base in the template is not complementary to the added dNTP, then no incorporation occurs and no hydrogen ion is released (and the output signal is then sometimes referred to as a "0-mer" output signal). In each wash step of the cycle, an unbuffered wash solution at a predetermined pH may be used to remove the dNTP of the previous step in order to prevent misincorporations in later cycles. Deliveries of nucleotides to a reaction vessel or chamber may be referred to as "flows" of nucleotide triphosphates (or dNTPs). For convenience, a flow of dATP will sometimes be referred to as "a flow of A" or "an A flow," and a sequence of flows may be represented as a sequence of letters, such as "ATGT" indicating "a flow of dATP, followed by a flow of dTTP, followed by a flow of dGTP, followed by a flow of dTTP. In an embodiment, the four different kinds of dNTP are added sequentially to the reaction chambers, so that each reaction is exposed to the four different dNTPs, one at a time. In an embodiment, the four different kinds of dNTP are added in the following sequence: dATP, dCTP, dGTP, dTTP, dATP, dCTP, dGTP, dTTP, etc., with each exposure, incorporation, and detection steps followed by a wash step. Each exposure to a nucleotide followed by a washing step can be considered a "nucleotide flow." Four consecutive nucleotide flows can be considered a "cycle." For example, a two cycle nucleotide flow order can be represented by: dATP, dCTP, dGTP, dTTP, dATP, dCTP, dGTP, dTTP, with each exposure being followed by a wash step. Different flow orders are of course possible. In various embodiments, the predetermined sequence or ordering may be based on a cyclical, repeating pattern of consecutive repeats of a predetermined reagent flow ordering (e.g., consecutive repeats of predetermined sequence of four nucleotide reagents such as "TACG TACG . . . "), or may be based on a random reagent flow ordering, or may be based on an ordering comprising in whole or in part a phase-protecting reagent flow ordering as described in Hubbell et al., U.S. patent application Ser. No. 13/440,849, filed Apr. 5, 2012, which is incorporated by reference herein in its entirety, or some combination thereof.

Figure 5:
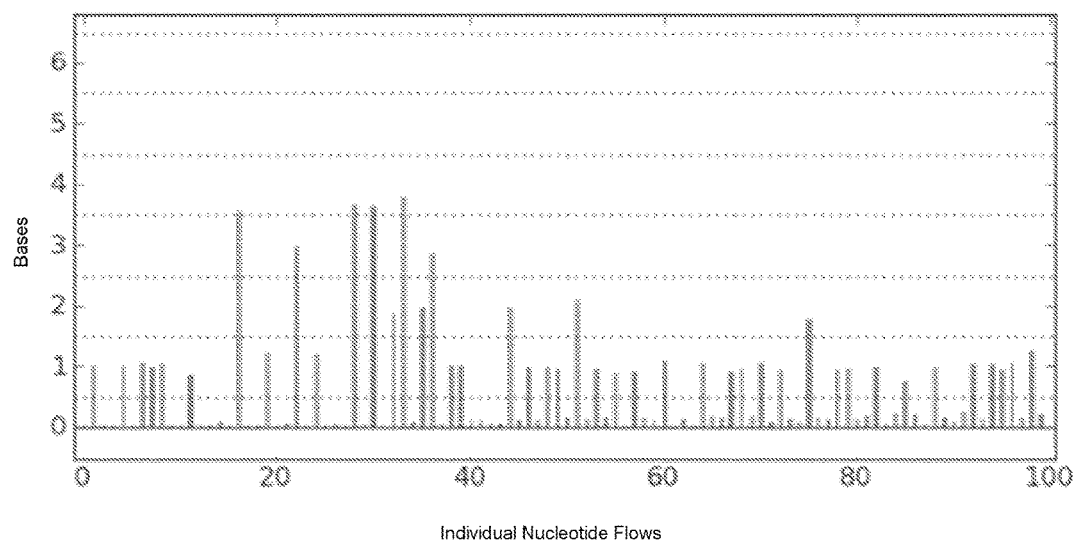
FIG. 5 shows an exemplary ionogram representation of signals from which base calls may be made.

FIG. 5 shows an exemplary ionogram representation of signals from which base calls may be made. In this example, the x-axis shows the nucleotide that is flowed and the corresponding number of nucleotide incorporations may be estimated by rounding to the nearest integer shown in the y-axis, for example. Signals used to make base calls and determine a flowspace vector may be from any suitable point in the acquisition or processing of the data signals received from sequencing operations. For example, the signals may be raw acquisition data or data having been processed, such as, e.g., by background filtering, normalization, correction for signal decay, and/or correction for phase errors or effects, etc. The base calls may be made by analyzing any suitable signal characteristics (e.g., signal amplitude or intensity).

In various embodiments, output signals due to nucleotide incorporation may be processed in various way to improve their quality and/or signal-to-noise ratio, which may include performing or implementing one or more of the teachings disclosed in Rearick et al., U.S. patent application Ser. No. 13/339,846, filed Dec. 29, 2011, and in Hubbell, U.S. patent application Ser. No. 13/339,753, filed Dec. 29, 2011, which are all incorporated by reference herein in their entirety.

In various embodiments, output signals due to nucleotide incorporation may be further processed, given knowledge of what nucleotide species were flowed and in what order to obtain such signals, to make base calls for the flows and compile consecutive base calls associated with a sample nucleic acid template into a read. A base call refers to a particular nucleotide identification (e.g., dATP ("A"), dCTP ("C"), dGTP ("G"), or dTTP ("T")). Base calling may include performing one or more signal normalizations, signal phase and signal droop (e.g., enzyme efficiency loss) estimations, and signal corrections, and may identify or estimate base calls for each flow for each defined space. Base calling may include performing or implementing one or more of the teachings disclosed in Davey et al., U.S. patent application Ser. No. 13/283,320, filed Oct. 27, 2011, which is incorporated by reference herein in its entirety. Other aspects of signal processing and base calling may include performing or implementing one or more of the teachings disclosed in Davey et al., U.S. patent application Ser. No. 13/340,490, filed on Dec. 29, 2011, and Sikora et al., U.S. patent application Ser. No. 13/588,408, filed on Aug. 17, 2012, which are all incorporated by reference herein in their entirety.

Figure 6A:
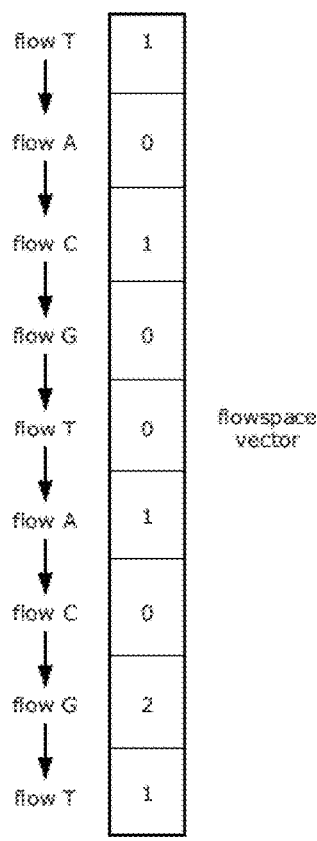
FIGS. 6A and 6B demonstrate a relationship between a base space sequence and a flowspace vector.
Figure 6B:
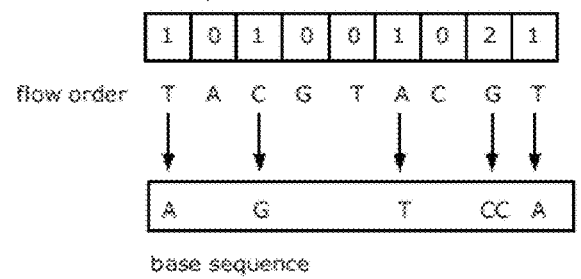

FIGS. 6A and 6B demonstrate a relationship between a base space sequence and a flowspace vector. A series of signals representative of a number of incorporations or lack thereof (e.g., 0-mer, 1-mer, 2-mer, etc.) produced by a series of nucleotide flows may be referred to as a flowspace vector or sequence, as opposed to a base space sequence, which is simply the order of identified nucleotide bases in a nucleic acid of interest. The flowspace vector may be produced using any suitable nucleotide flow ordering, including a predetermined ordering based on a cyclical, repeating pattern of consecutive repeats of a predetermined reagent flow ordering, based on a random reagent flow ordering, or based on an ordering comprising in whole or in part a phase-protecting reagent flow ordering as described in Hubbell et al., U.S. patent application Ser. No. 13/440,849, filed Apr. 5, 2012, or some combination thereof. In FIGS. 6A and 6B, an exemplary base space sequence AGTCCA is subjected to sequencing operations using a cyclical flow ordering of TACG (that is, a T nucleotide flow, followed by an A nucleotide flow, followed by a C nucleotide flow, followed by a G nucleotide flow, and this 4-flow ordering is then repeated cyclically). The flows result in a series of signals having an amplitude (e.g., signal intensity) related to the number of nucleotide incorporations (e.g., 0-mer, 1-mer, 2-mer, etc.). This series of signals generates the flowspace vector 101001021. As shown in FIG. 6A, the base space sequence AGTCCA may be translated to a flowspace vector 101001021 under a cyclical flow ordering of TACG. The flowspace vector may change if the flow ordering is changed. As shown in FIG. 6B, the flowspace vector may be mapped back to the base space sequence associated with the sample.

Barcodes

In various embodiments, sample discriminating codes or barcodes may comprise or correspond to or with (whether directly or indirectly) sequences of nucleotides, biomolecule components and/or subunits, or polymer components and/or subunits. In an embodiment, a sample discriminating code or barcode may correspond to a sequence of individual nucleotides in a nucleic acid or subunits of a biomolecule or polymer or to sets, groups, or continuous or discontinuous sequences of such nucleotides or subunits. In an embodiment, a sample discriminating code or barcode may also correspond to or with (whether directly or indirectly) transitions between nucleotides, biomolecule subunits, or polymer subunits, or other relationships between subunits forming a sample discriminating code or barcode.

In various embodiments, sample discriminating codes or barcodes may have properties that permit them to be read, or otherwise recognized, identified, or interpreted with improved accuracy and/or reduced error rates for a given code type, length, or complexity. In an embodiment, a sample discriminating code or barcode may be designed as a set (which may include subsets) of individual sample discriminating codes or barcodes. In some embodiments, one or more sample discriminating codes or barcodes in a set (or in a subset from that set) may be selected based on one or more criteria to improve accuracy and/or reduce error rates in reading, or otherwise recognizing, identifying, discriminating, or interpreting the codes.

In various embodiments, sample discriminating codes or barcodes may be designed to exhibit high fidelity reads, which may be assessed based on empirical sequencing measurements. The level of fidelity may be based on predictions of the read accuracy of a sample discriminating code or barcode having a particular nucleotide sequence. Certain nucleotide sequences known to cause sequencing read ambiguity, errors, or sequencing bias may be avoided. Design may be based on accurately calling the sample discriminating code or barcode (and associated sample or nucleic acid population), even in the presence of one or more errors. In various embodiments, fidelity may be based on the probability of correctly sequencing the sample discriminating code or barcode, which may be at least 82%, or at least 85%, or at least 90%, or at least 95%, or at least 99%, or more.

In various embodiments, sample discriminating codes or barcodes may be designed to exhibit improved read accuracy for sequencing using a sequence-by-synthesis platform (as discussed previously), which may include fluorophore-labeled nucleotide sequencing platforms or non-labeled sequencing platforms, such as the Ion PGM™ and Ion Proton™ Sequencers, for example. Design of the sample discriminating codes or barcodes and specific sequences are not limited to any particular instrument platform or sequencing technology, however. In the case of non-nucleic acid codes, sample discriminating codes or barcodes may be read, identified, interpreted or otherwise recognized using methods known in the art, including for example, amino acid sequencing for protein sample discriminating codes.

In various embodiments, sample discriminating codes or barcodes may be designed to optimize the barcode's observed performance in a sequencing process. A design approach may include applying a series of sample discriminating code or barcode constraints or criteria to achieve desired properties or performance. Such constraints or criteria may include one or more of uniqueness of nucleic acid barcode sequences and a degree of separation from other nucleic acid barcode sequences. A set of barcodes may be a nested set of barcodes, which may be based on one or more design criteria. In an embodiment, nested barcode sets may be designed analogously to Matryoshka nesting, such that the properties of a subset are entirely contained within the properties of a genus set. For example, a first subset of barcodes meeting certain properties (e.g., a high sequencing fidelity) may be selected from a larger set of barcodes meeting the same properties. For example, if a set of barcodes comprises 96 uniquely identifiable barcodes, then a subset of 16 barcodes may be selected from the 96 available barcodes for a sequencing experiment comprises only 16 multiplexed samples. The subset of 16 barcodes may thus be optimized to a similar degree as a larger subset of 32 barcodes or 48 barcodes selected from the full set of 96 barcodes. In an embodiment, the barcodes may be designed as an ordered list of nested barcodes. In an embodiment, the barcodes (e.g., a set of 96) may be ordered by having a first barcode, a second barcode that is the one (of the remaining 95) that is furthest from the first one under a suitable distance measure, a third barcode that is the one (of the remaining 94) that is furthest from the first and second one under a suitable distance measure, and so on until all the barcodes have been ordered. A user may then select an appropriate number of barcode from such an ordered list.

In various embodiments, sample discriminating codes or barcodes may contain a target sequence that is a sequence of interest, and in such cases may assist in uniquely identifying or discriminating different target sequences. The target sequence may be any type of sequence from any source of interest, including amplicons, candidate genes, mutational hot spots, single nucleotide polymorphisms, genomic library fragments, etc., for example. The sample discriminating code or barcode sequence may be operatively coupled to the target sequence at any of various points in the sample preparation process using techniques such as PCR amplification, DNA ligation, bacterial cloning, etc., for example. The sample discriminating code or barcode sequence may be contained in oligonucleotides and ligated to genomic library fragments using any suitable DNA ligation technique.

In various embodiments, sample discriminating codes or barcodes may have various lengths, which may be selected based on a number of samples to be identified. In various embodiments, for a 16-sample multiplexed sequencing experiment, 16 uniquely identifiable barcodes may be sufficient to uniquely identify each sample. Similarly, for a 64- or 96-sample multiplexed sequencing experiment, for example, only 64 or 96 barcodes may be sufficient, respectively. Larger numbers of samples may require longer codes. However, although longer codes will allow identification of a larger number of samples, they may have drawbacks. For example, in sequencing-by-synthesis, longer codes may require additional numbers of nucleotide flows, which may decrease accuracy given that sequencing tends to be maximally accurate in earlier flows, where the codes may typically be located. In various embodiments, nucleic acid barcodes, for example, may have a length of about 4-30 bases, or about 4-50 bases, or more, for example. The length may be selected based on one or both of a length of the probe sequence and a number of samples in the experiment. The length may be a multiple of the probe sequence length. The length may be longer for a larger number of samples. For example, in a 16-sample experiment using 5-base probe sequences, the barcodes may be 5 bases in length; and in a 96-sample experiment using 5-base probe sequences, the barcodes may be 10 bases in length.

In various embodiments, sample discriminating codes or barcodes may be designed based on one or more of the considerations and/or criteria set forth above (which may be taken alone or in combination). For example, a set of nucleic acid barcodes may be designed such that problematic sequences are avoided in all positions. In another example, a set of nucleic acid barcodes may be designed such that problematic sequences are avoided and the nucleic acid barcodes are sequenced with high fidelity. Various combinations of considerations/criteria may be chosen based on the sequencing experiment. For example, if barcodes are to be used for a small number of samples, the barcodes may not necessarily be designed to have nested subsets. The design considerations/criteria may be selected based on the number of samples, the level of accuracy needed, the sensitivity of the sequencing instrument to detect individual samples, the accuracy of the sequencing instrument, etc., for example.

In various embodiments, sample discriminating codes or barcodes may be designed to have error-tolerant properties. The error-tolerant properties may be in base space (in other words, the errors here may related to incorrect bases in the barcode, such as, e.g., a "C" base present where a "T" base should be in the barcode). For example, a 1-base error-tolerant barcode set may be designed such that if a sequencing error is encountered at any position in one or more barcodes of the set each barcode may still be resolvable from other barcodes in the set (e.g., the set may be such that if one base is incorrect in a given erroneous barcode, that erroneous barcode may still be resolved from the other barcodes in the set because they all differ from the erroneous barcode in at least two base locations, for example, so that if the error occurred at one of these two locations, the other remains available to allow distinction between the barcodes). The set may also be designed to be able to distinguish barcodes within it even where multiple errors (e.g., 2, 3, etc.) in one or more of the barcodes are encountered. Such error-tolerant properties are advantageous as they help provide more certainty for resolving even complex multiplexed samples, even in the presence of potential sequencing errors. Candidate barcodes in a set may be compared to ascertain error-tolerant properties. For example, such barcodes can be compared (e.g., via computer analysis or simulation) to determine whether, if any one error (or 2, 3, etc., as the criterion may be) occurred, the codes can still be distinguished.

In various embodiments, sample discriminating codes or barcodes as set forth herein may be used in any suitable manner to assist in identifying or resolving samples. For example, barcodes may be used individually, or two or more barcodes may be used in combination. In an embodiment, a single barcode may identify one target sequence or multiple target sequences. For example, a single barcode may identify a group of target sequences. A barcode may be read separately from the target sequence or as part of a larger read operation spanning the barcode and a target sequence. The barcode may be positioned at any suitable position within the sample, including before or after a target sequence.

Barcode Design & Flowspace

In various embodiments, sample discriminating codes or barcodes may be designed at least partly based on flowspace considerations, rather than base space. In other words, design may be based at least partly on flowspace vectors rather than base sequences. For example, sample discriminating codes or barcodes may be designed based on projection into flowspace as a flowspace vector under a selected or predetermined flow ordering. A string of characters in the flowspace vector of a barcode (e.g., a string of digits or characters such as 0, 1, 2, etc., that may represent a non-incorporation, a 1-mer incorporation, a 2-mer incorporation, etc., responsive to flows of nucleotide flowed or introduced according to a predetermined ordering) may represent or correspond to a codeword of an error-tolerant code (e.g., an error-correcting code). In an error-correcting code, a string of characters may be such that errors introduced into the string (e.g., during sequencing) can be detected and/or corrected based on remaining characters in the string. An error-correcting code may be made up of a set of different character strings, which may be referred to as codewords, over a given finite alphabet E of character elements. A codeword may be viewed as comprising a message plus some redundant data or parity data allowing a decoder to correctly decode a codeword containing one or more errors. Codewords may be designed to be sufficiently separated from one another to allow for a permissible numbers of errors to be detected in the transmission of a codeword and, in some cases, to be corrected by calculating which actual codeword is closest to the received codeword. In sequencing-by-synthesis, for example, a message string may be considered "transmitted" when a barcode has been sequenced and projected into flowspace as a flowspace string.

In various embodiments, sample discriminating codes or barcodes may be designed using any suitable type of error-correcting code. The error-correcting code may be a linear block code using an alphabet E of character elements with each codeword having n encoding character elements. Redundancy and/or parity data may be added to the message to allow a receiver to detect and/or correct errors in a transmitted codeword, and to recover the original message using a suitable decoding algorithm.

In various embodiments, sample discriminating codes or barcodes may be designed using various numbers of character elements in a code alphabet, which may vary according to a particular application. The error-correcting code may be a binary code using an alphabet of two character elements. The error-correcting code may be a ternary code using an alphabet of three character elements. In an embodiment, the number of characters elements may depend on a length of a longest homopolymer run allowed in the barcode sequence. For example, if a barcode has only 1-mers (no repeating bases), then the error-correcting code may be a binary code with one character to represent a non-incorporation and another character to represent a single-base incorporation (e.g., an alphabet E for such a binary code may be {0, 1}, with "0" representing a non-incorporation and "1" representing a single-base incorporation). In another example, if the barcode has only 1-mers and 2-mers, then the error-correcting code may be a ternary code with the same non-incorporation and single-base incorporation characters, and a third character to represent a two-base incorporation (e.g., an alphabet E for such a ternary code may be {0, 1, 2}, with "2" representing a two-base incorporation). The size and the set of characters used in other code alphabets may be suitably modified if the barcode sequence has 3-mers, 4-mers, and so on.

In various embodiments, sample discriminating codes or barcodes may be designed using an error-correcting code based at least in part on Hamming codes, Golay codes, and/or tetracode codes. In an embodiment, the error-correcting code may be a binary Hamming code. In another embodiment, the error-correcting code may be a binary Golay code. In an embodiment, the error-correcting code may be a ternary Hamming code. In another embodiment, the error-correcting code may be a ternary Golay code. See, e.g., Hoffman et al., Coding Theory: The Essentials, Marcel Dekker, Inc. (1991); and Lin et al., Error Control Coding: Fundamentals And Applications, Prentice Hall, Inc. (1983).

In various embodiments, sample discriminating codes or barcodes may be designed to have error-tolerant properties expressed in flowspace rather than in base space (in other words, the errors here may related to incorrect digits or characters in the flowspace representation of the barcode, e.g., an erroneous "0" or "0-mer" present where a "1" or "1-mer" should be in the flowspace representation). For example, a 1-base (in flowspace) error-tolerant barcode set may be designed such that if a sequencing error is encountered at any position in the flowspace representation in one or more barcodes of the set each barcode may still be resolvable from other barcodes in the set because their flowspace representations all differ from the erroneous barcode(s) in at least two digit locations, so that if the error occurred at one of these two digit locations, the other remains available to allow distinction between the barcodes. The set may also be designed to be able to distinguish barcodes within it even where multiple errors in flowspace (e.g., 2, 3, etc.) in one or more of the barcodes are encountered. Such error-tolerant properties are advantageous as they help provide more certainty for resolving even complex multiplexed samples, even in the presence of potential sequencing errors. Candidate barcodes in a set may be compared to ascertain error-tolerant properties in flowspace. For example, such barcodes can be compared (e.g., via computer analysis or simulation) to determine whether, if any one error in flowspace (or 2, 3, etc., as the criterion may be) occurred, the codes can still be distinguished.

In various embodiments, sample discriminating codes or barcodes may be designed using one or more distance measures capable of evaluating a distance between codewords. In an embodiment, the distance measure may be a Hamming distance, which corresponds to the number of positions at which two codewords differ. Mathematically, if each codeword in a set of codewords has a Hamming distance of at least d from all other codewords in the set, then the code can correct up to $(d-1)/2$ errors, or conversely, the Hamming distance d required to decode up to x number of errors is $2x+1$. The quantity d may be referred to as the minimum distance of the code. The notation [n, k, d] may be used to characterize an error-correcting code of length n digits that encodes k information digits and has a minimum distance d. Other distance measures may be used, including a Euclidean distance measure, a sum of absolute values of differences between corresponding entries of two codewords, and a sum of squared differences between corresponding entries of two codewords, for example. In various embodiments, using such distance measures can allow a distance between codewords to be evaluated in flowspace, without a need for base calls to be made.

In various embodiments, sample discriminating codes or barcodes may be designed to have an error-correcting code with a minimum distance of five that is capable of correcting up to two digit errors in the codewords (such as, e.g., an erroneous "0" or "0-mer" present where a "1" or "1-mer" should be at a first location and, e.g., an erroneous "0" or "0-mer" present where a "2" or "2-mer" should be at a second location in the flowspace representation). In other words, each codeword may have a Hamming distance of at least five from all other codewords. In another embodiment, the error-correcting code may have a minimum distance of three and be capable of correcting a single digit error in the codewords. In other words, each codeword may have a Hamming distance of at least three from all other codewords. In an embodiment, an algorithm or methodology that iteratively compares each codeword in a candidate group to all others in the group to construct a largest codeword set that maintains the desired minimum distance and has the desired error-correcting capability may be used.

In various embodiments, sample discriminating codes or barcodes may be designed to distinguish reads in flowspace rather than base space, which may be particularly useful in sequencing-by-synthesis and may help avoid an excessive number of flows and thereby reduce error build-up and wasted/diminished sequencing capacity. The Hamming distance, for example, may not be desirable in base space. For example, a single base insertion at the beginning of a sequence (e.g., AACGT vs. ACGT) would yield a Hamming distance of 3 (based on the first four bases, to have equal length) despite an in/del distance of only 1. Further, when translating a binary code into 4 letters by paired bits, errors automatically affect two bits simultaneously, and an error correction of 1 bit is not guaranteed to correct 1 error in base reading. Furthermore, conventional barcode designs may not appropriately address sequencing error motifs. In an embodiment, codewords may be selected for useful biological properties.

In various embodiments, sample discriminating codes or barcodes may be designed for one error or two errors correction in flowspace to correct flowspace errors such as, e.g., insertions and deletions. The barcodes may collectively be designed to be tolerant of single errors in flowspace. A subset of the barcodes may be designed to correct a single flowspace error. The barcodes may further be divided into subsets that, when used alone, may correct for multiple flowspace errors (e.g., two or more errors). This may allow for a set of 96 barcodes or more, for example, that can correct two flowspace errors. The barcode set may be generated using a ternary coding scheme in flowspace (e.g., in flowspace, the barcodes may be viewed as having either 0, 1, or 2 incorporation(s) in a given flow).

In various embodiments, sample discriminating codes or barcodes may be designed around a Hamming ternary code mapped into a particular predetermined flow ordering. For example, such a code may be a [n=13, k=10, d=3] Hamming ternary code; and such a mapping may take the first 10 "trits" (e.g., symbols of the ternary code, such as 0, 1, and 2, for example) and assign them to some of the flows in the predetermined ordering (e.g., flows 9-18), and take three "parity check" trits and assign them to other flows (e.g., 19-21). A final synchronization flow may then be a 1-mer (e.g., a 'C' at flow 22) to result in the flows terminating the codeword being zero if they are specified to be zero. Some of the codewords generated under the Hamming codes may not be permissible flowspace representations (e.g., they may be valid mathematical codewords in flowspace that do not correspond to a possible nucleic acid sequence in base space given the predetermined flow ordering). These codewords may be filtered out. In some embodiments, the codewords may be further filtered to include only codewords composed of a desired length (9-15 bases, for example).

In various embodiments, sample discriminating codes or barcodes may be designed around an [n=11, k=6, d=5] ternary Golay code using values 0, 1, and 2. Such a code has 729 (i.e., $3^6$) distinct codewords of length 11 with a distance of 5 between the codewords to correct 2 errors. The codewords may be generated linearly or cyclically or using any suitable methods. As with the Hamming code, some of the codewords generated under the ternary Golay code may not correspond to a possible nucleic acid sequence in base space given the predetermined flow ordering and can thus be filtered out.

Figure 7A:
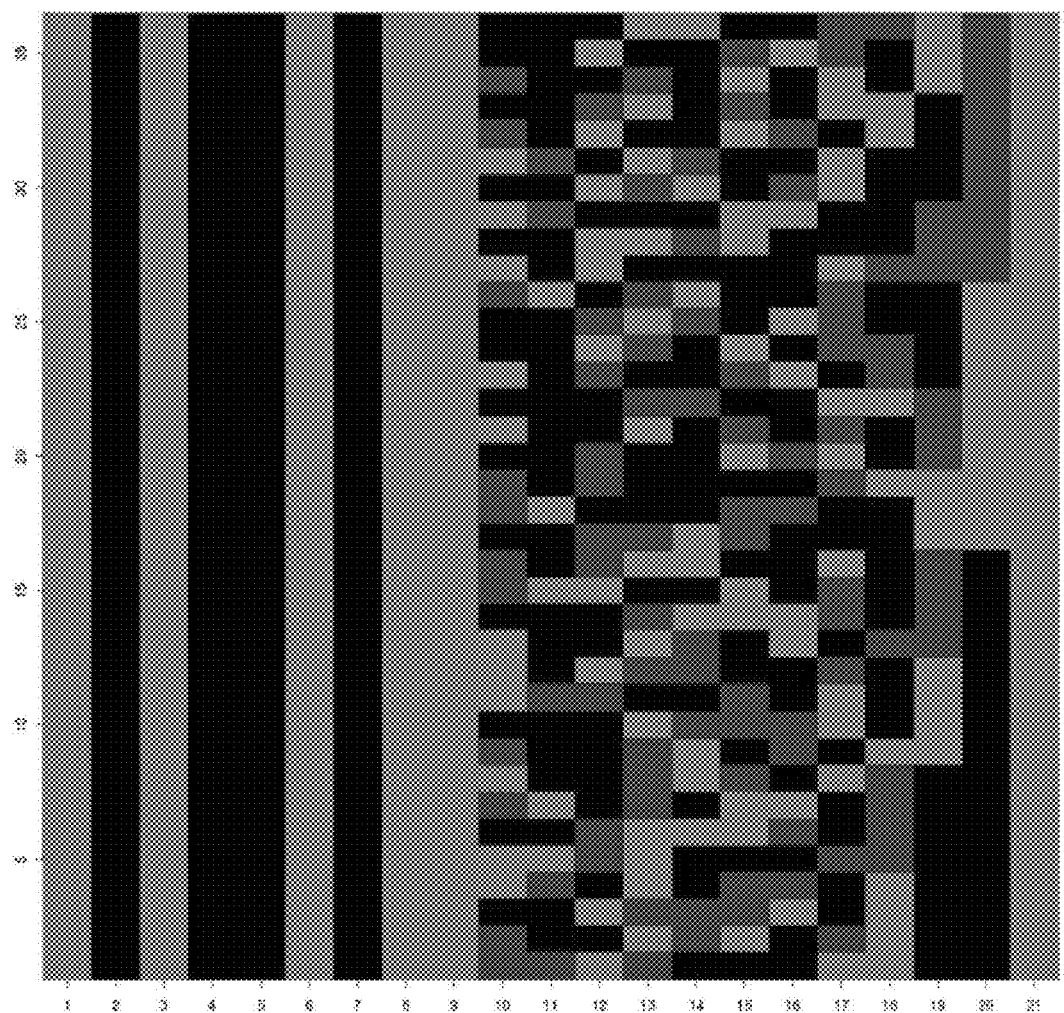
FIG. 7A illustrates an exemplary translation to flowspace of 36 9-mer ternary Golay codewords permissible under a predetermined flow ordering.

FIG. 7A illustrates an exemplary translation to flowspace of 36 9-mer ternary Golay codewords permissible under a predetermined flow ordering. The x-axis corresponds to the first 21 flows of a predetermined flow ordering (in this case, TACG, followed by TACG, followed by TCTG, followed by AGCA, followed by TCGA, followed by T (with the remaining flows in that ordering being CGA, followed by TGTA, followed by CAGC)). The y-axis corresponds to homopolymer responses to these flows, reflecting 36 permissible ternary Golay codewords. The color/gray coding indicates the code symbols (black is 0 for a 0-mer, red or light gray is 1 for a 1-mer, and blue or dark gray is 2 for a 2-mer). For example, the sequence of 1-mer(s) and 2-mer(s) in the first line (i.e., bottom row) corresponds to T (1-mer responsive to flow 1 of T), followed by C (1-mer responsive to flow 3 of C), followed by A (1-mer responsive to flow 6 of A), followed by G (1-mer responsive to flow 8 of G), followed by T (1-mer responsive to flow 9 of T), followed by CC (2-mer responsive to flow 10 of C), followed by TT (2-mer responsive to flow 11 of T), followed by G (1-mer responsive to flow 12 of G), followed by AA (2-mer responsive to flow 13 of A), followed by T (1-mer responsive to flow 17 of T), followed by C (1-mer responsive to flow 18 of C), followed by T (1-mer responsive to flow 21 of T). In each line, there are 5 base key TCAGT (corresponding to flows 1-9), 11 flows of code (a permissible Golay codeword in each line in flows), and 1 flow to resynchronize (flow 21 of T). One may use the existing 11-base codewords in the Ternary Golay code to fill in flowspace. Every line differs from any other line in at least five flows. As mentioned previously, there are 729 (i.e., $3^6$) Golay codewords of length 11 in flowspace (e.g., sequences of eleven characters selected from 0, 1, or 2) and, as illustrated in FIGS. 6A and 6B, a flowspace representation may be mapped into a base sequence given a predetermined flow ordering. In base space, there are 262,144 possible sequences of nine bases selected from A, C, G, or T (i.e., $4^9$). However, not every one of the possible Golay codewords in flowspace corresponds to one of the possible sequences in base space under a given predetermined flow ordering. Codewords that do not correspond to a permissible sequence may be filtered out. A computer analysis and/or simulation may be performed to determine which flowspace codewords, for a given predetermined flow ordering, correspond to a possible sequence of bases in base space.

Figure 7B:
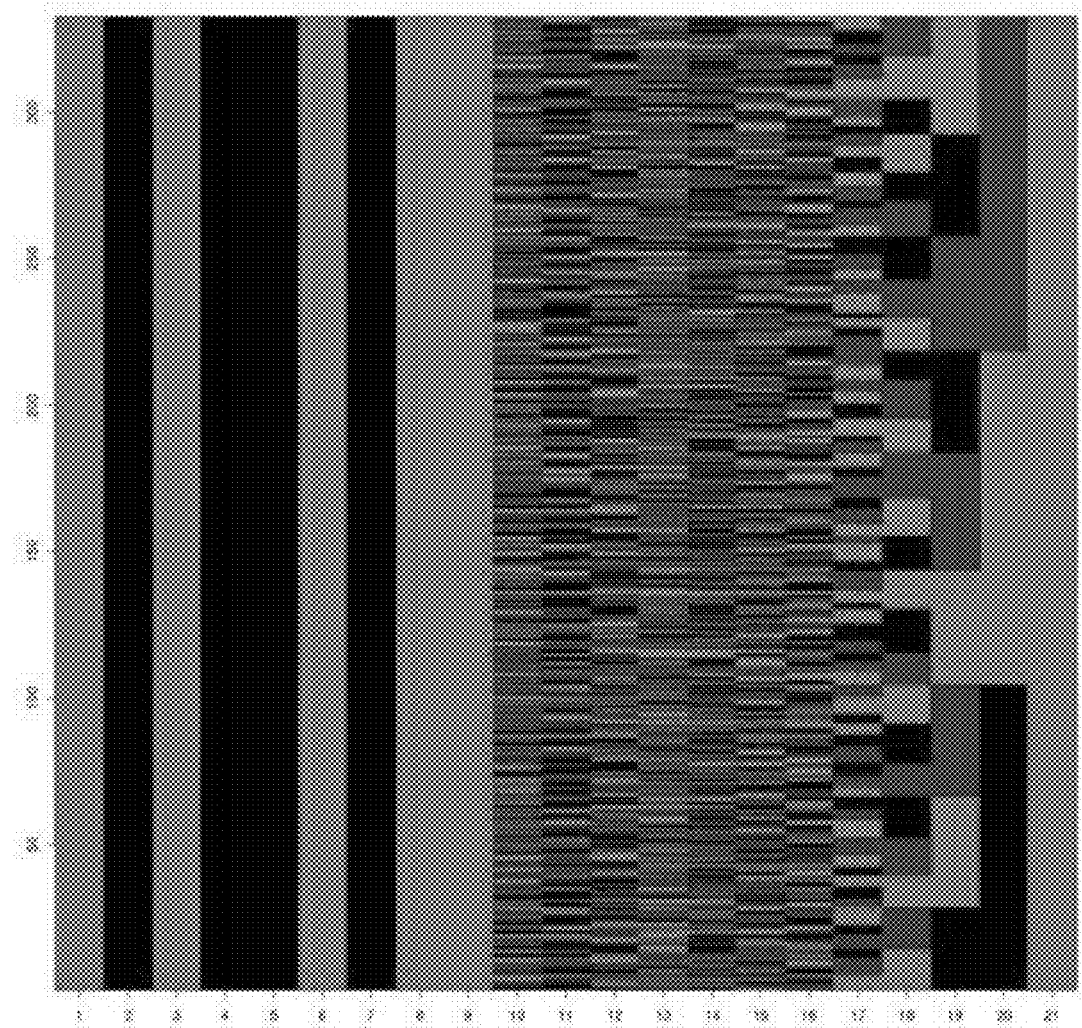
FIG. 7B illustrates an exemplary translation to flowspace of 332 ternary Golay codewords permissible under the same predetermined flow ordering as in FIG. 7A.

FIG. 7B illustrates an exemplary translation to flowspace of 332 ternary Golay codewords permissible under the same predetermined flow ordering as in FIG. 7A. The graph is essentially the same as in FIG. 7A, except that the permissible Golay codewords are not limited to 9-mer ones. In other words, of the 729 possible [11, 6, 5] codewords, which have length 11 in flowspace (a property of this particular code), these are the codewords that correspond to a base space sequence that is possible (e.g., that could actually occur) under the predetermined flow ordering of FIG. 7A. Of course, this particular set of codewords is just an example, and different ones would arise for that ternary Golay code with a different predetermined flow ordering.

Figure 7C:
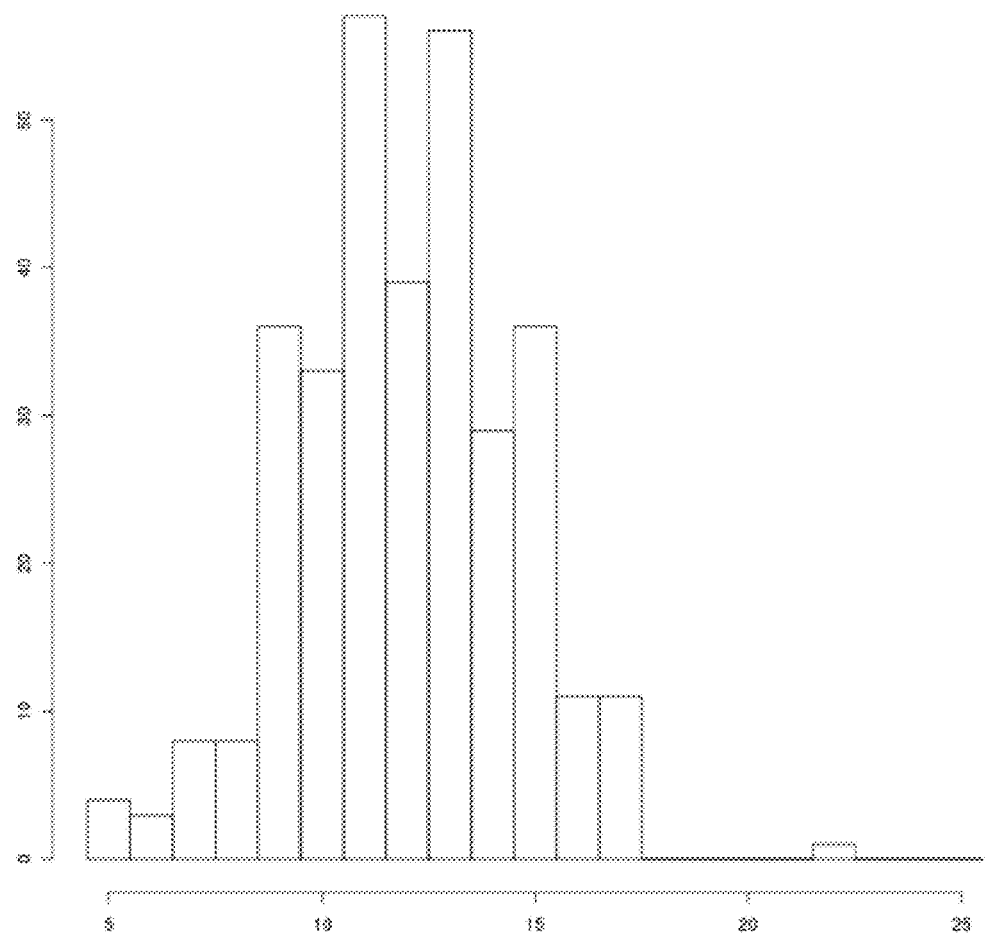
FIG. 7C illustrates exemplary Golay flowspace barcode weights for the codewords represented in FIG. 7A.

FIG. 7C illustrates exemplary Golay flowspace barcode weights for the codewords represented in FIG. 7A. The x-axis shows the number of bases in each codeword. The y-axis shows the corresponding frequency. For example, there are 36 9-mers, 33 10-mers, 57 11-mers, etc. The codewords are separable under the predetermined flow ordering in FIGS. 7A and 7B, and no particular Hamming distance in base space was applied as constraint (in other words, that distance in base space need only be at least 1).

In various embodiments, sample discriminating codes or barcodes may be designed around a tetracode code, in which codewords have length 4. There are 8 nonzero codewords (which may take values 0, 1, or 2), and they can correct 1 error (and detect 2 errors).

Figure 8A:
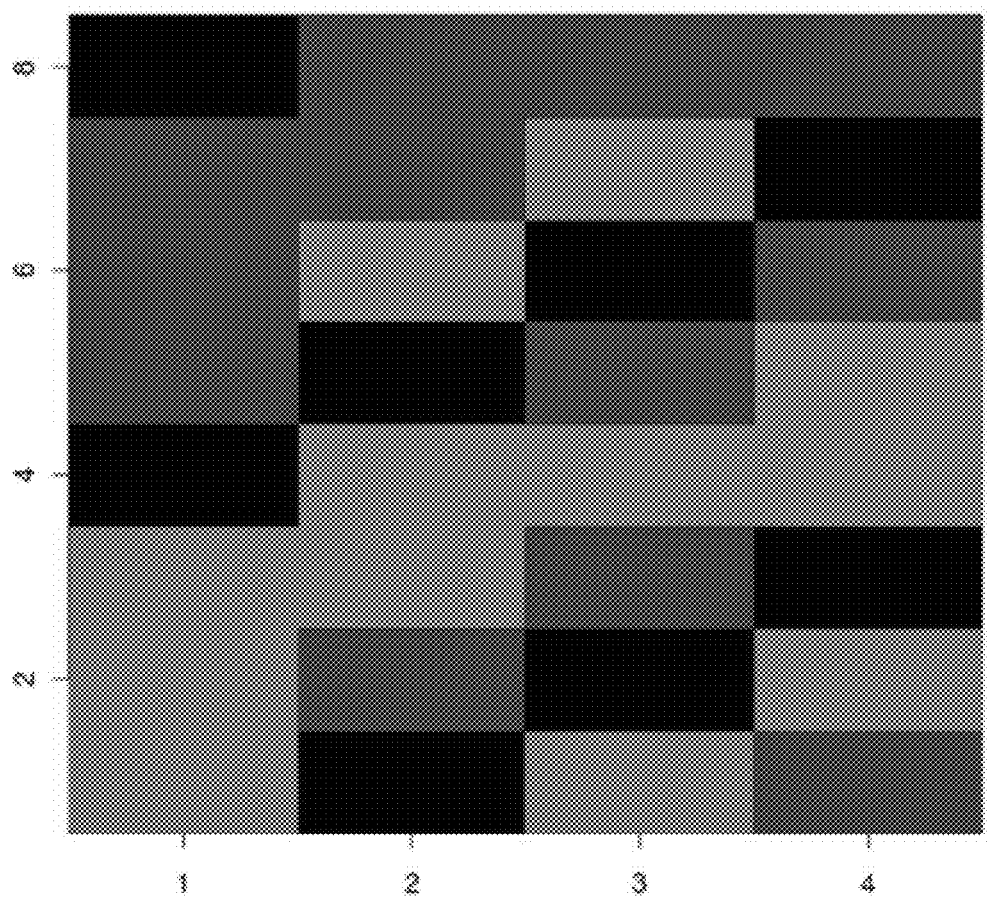
FIG. 8A illustrates 8 nonzero ternary tetracode codewords.

FIG. 8A illustrates 8 nonzero ternary tetracode codewords. The x-axis shows the position in the codeword. The y-axis shows each codeword. Color/gray coding indicates the code symbols (black is 0 for a 0-mer, red or light gray is 1 for a 1-mer, and blue or dark gray is 2 for a 2-mer). Such codewords are always permissible in a (repeating) 4-base flow order XYZW.

Figure 8B:
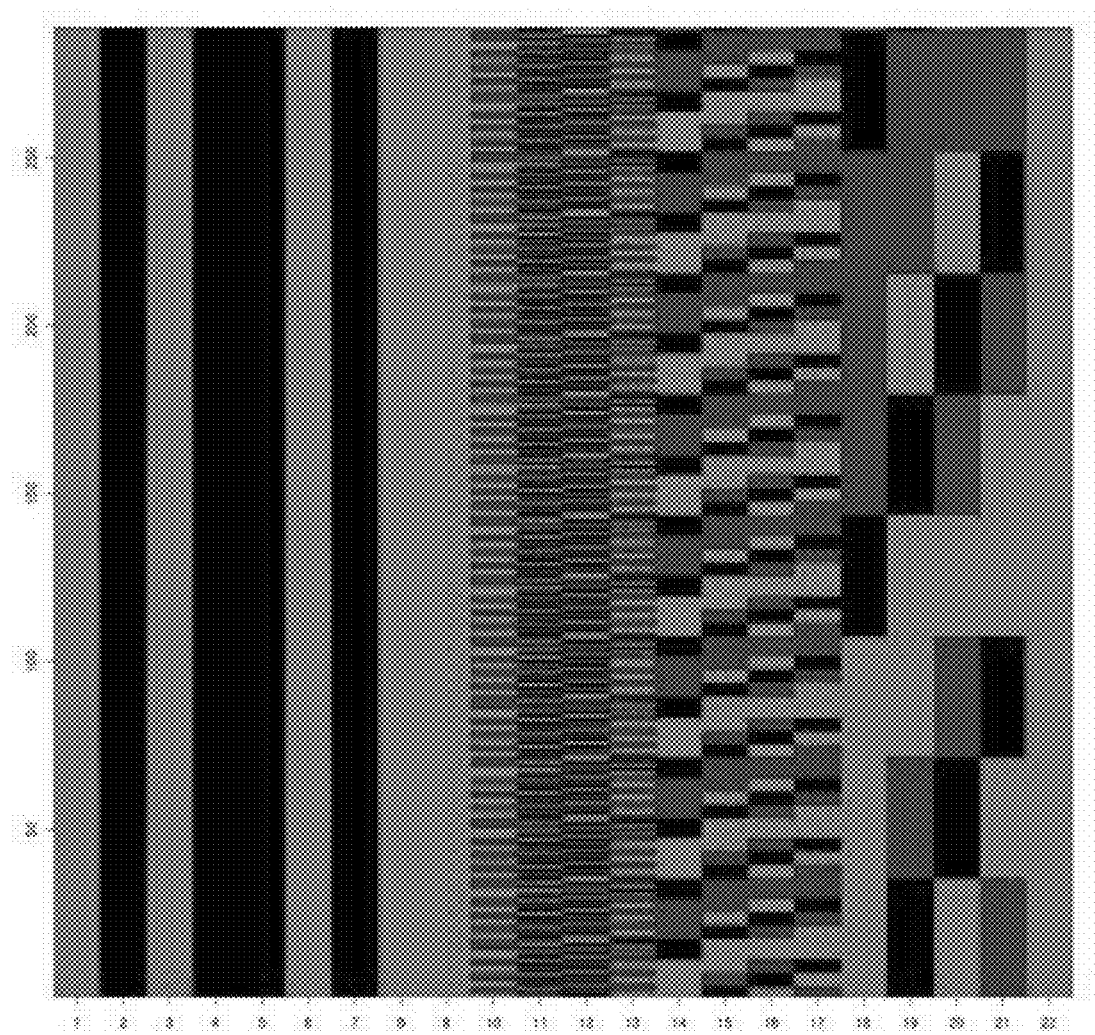
FIG. 8B illustrates 288 nonzero ternary concatenated tetracode codewords permissible under the same predetermined flow ordering as in FIG. 7A.

FIG. 8B illustrates 288 nonzero ternary concatenated tetracode codewords permissible under the same predetermined flow ordering as in FIG. 7A. The x-axis shows the flow number. The y-axis shows each codeword. In each line, there are 5 base key TCAGT (corresponding to flows 1-9), 12 flows of code (3 concatenated tetracode codewords), and 1 flow to resynchronize (flow 22 of C). Here, not all flow sequences are permissible because of interactions.

According to an embodiment, there is provided a method for generating barcodes, comprising: designing codewords based on a predetermined flow order and using a ternary code, wherein the codewords (1) are expressed in flowspace; (2) include 0-mer(s), 1-mer(s), or 2-mer(s) only; (3) can correct 2 flowspace errors; and (4) are permissible flowspace sequences that correspond to base space sequences that are possible given the predetermined flow order. The ternary code may be a Hamming code, a Golay code, and a tetracode code, for example. The barcodes may be compact in flowspace (e.g., post-key all barcodes may be designed to end at flow 21, with a length 11 ternary code, and a 5-base key); and may have a buffer base at flow 21.

Barcodes as described herein may be particularly useful for sequencing-by-synthesis methods that operate by unterminated single-nucleotide addition, in which the precursor nucleotides are repeatedly added individually to the reaction in series according to a predetermined ordering (such as, e.g., methods based on hydrogen ions produced by the incorporation reactions or on the detection of inorganic pyrophosphate, which may be detected by light emitted from an enzyme cascade initiated by the inorganic pyrophosphate). In such methods, errors of insertions and/or deletions may arise due to inaccurate base-calling in flowspace. For example, in the sequence ACCGT, the C base 2-mer may be incorrectly called as a 1-mer in flowspace, resulting in the omission (deletion) of a C base in the sequence read (in other words, that sequence could be incorrectly read as ACGT). Barcodes as described herein may be particularly useful for detecting and/or correcting such read errors.

Various algorithms and/or software tools may be used to assist in the generation of error-correcting codes. A number of different design considerations may factor into the development of a coding strategy. As explained above, a barcode sequence and a flowspace codeword have a mapping relationship to each another for a given flow ordering. Thus, design or selection criteria with respect to the barcode sequence may be translated into corresponding design/selection criteria for the flowspace coding. Likewise, design/selection criteria with respect to the flowspace coding may be translated into corresponding design/selection criteria for the barcode sequence.

In various embodiments, the size of an error-correcting code (e.g., the number of codewords) may be varied as needed. A larger code is generally more constrained and difficult to construct, but may accommodate a larger number of multiplex samples. In an embodiment, the error-correcting code may contain at least 16 different codewords; or at least 32 different codewords; or at least 48 different codewords; or at least 96 different codewords; or more, for example. Because codewords and barcode sequences are related by flow mapping, these embodiments may translate to at least 16 different barcode sequences; or at least 32 different barcode sequences; or at least 48 different barcode sequences; or at least at least 96 different barcode sequences; or more, for example. Generally, the size of a code becomes smaller as the minimum distance of the code is increased, and such a code generally may accommodate fewer multiplex samples but with a better error-correcting capability. An appropriate balance between the error-correcting capability of the code and the size of the code may be considered in the code design.

In various embodiments, the length of flowspace codewords may be varied as needed. For example, if a larger code set (e.g., with more codewords) is needed, the length of the codewords may be increased. In an embodiment, the flowspace codewords may have a length of 15 or fewer digits, for example. In some embodiments, the flowspace codewords may have a length of four, which can be constructed of eight non-zero codewords that can detect two errors or correct one error. Other factors that may be considered include a desired error-correcting capability (e.g., the number of errors that the code can correct) and a decoding complexity (e.g., the computational time needed to decode each codeword). Also, flowspace codewords that do not correspond to any valid sequence under the predetermined flow ordering (e.g., in a cyclical four-nucleotide flow ordering, codewords having four 0's in a row) may be excluded.

In various embodiments, the length of the barcode sequences (or number of nucleotide bases) may be varied as needed. In an embodiment, the length may be limited to improve sequencing efficiency. In various embodiments, the barcode sequences may have a length of 20 or fewer bases; or in the range of 5-15 bases, for example. In various embodiments, the length of homopolymer runs in the barcodes may be limited to be compatible with the flowspace coding scheme. In some embodiments, the barcode sequences may contain only 1-mers (that is, no repeating bases), and the error-correcting code may then be a binary code. In some embodiments, the maximum length of homopolymer runs may be 3-mers or 2-mers, and the error-correcting code may then be a quaternary code or a ternary code, respectively.

In various embodiments, one or more molecular biology properties of nucleotide base sequences may be considered in the design or selection of barcode sequences. For example, the barcode sequences may be designed or selected to avoid certain nucleotide sequences known to cause sequencing read errors or result in sequencing bias. This can enhance PCR and/or sequencing performance. In some embodiments, because the GC (guanine/cytosine) content of a sequence can affect sequencing quality, barcode sequences having a GC content in the range of 40-60% may be preferred and barcodes outside this range may be filtered out. The AT content may also be similarly treated. In some cases, barcode sequences that are self-complementary or complementary with a primer sequence that is coupled to the barcode may be excluded.

An exemplary set of nucleic acid barcodes may be found in Appendix I of U.S. Prov. Pat. Appl. No. 61/529,687, filed Aug. 31, 2011, which is incorporated by reference herein in its entirety. Such nucleic acid barcodes (including various combinations, sub-combinations, and portions thereof), may be used, for example, in a multiplexed sequencing experiment with different samples.

In an embodiment, for a multiplex sequencing problem requiring a set of 96 barcodes that can correct two errors in the flowspace string, with some accommodation for potential loss due to poorly behaving barcodes, and a predetermined flow ordering of TACG, followed by TACG, followed by TCTG, followed by AGCA, followed by TCGA, followed by TCGA, followed by TGTA, followed by CAGC, for example, a set of barcode sequences may be generated using a ternary Hamming code of 13-digit length, with ten of the digits being treated as data and three of the digits being treated as parity checks in the codeword. This particular coding scheme yields about 140 codewords that can correct up to two errors. A representative sampling of this particular coding scheme is shown in Table 1 below. (A complete list of the barcodes and flowspace codewords generated can be seen in Appendix 1 of U.S. Pat. Appl. No. 61/529,687, filed Aug. 31, 2011, which is incorporated by reference herein in its entirety.) In this example, the barcodes were selected for those having 9-11 bases in length and were designed for use in oligonucleotides for multiplex sequencing on an Ion PGM™ sequencing instrument. The oligonucleotides for this example contained, in the following order, a primer site, a TCAG key sequence for quality control and sample detection, a unique barcode sequence, a common C base at the 3' end of the barcode sequences for synchronization to ensure that flows terminating the codeword are zero if they are specified to be zero, and a GAT buffer between the barcode and the insert to minimize the influence of the variable barcode region on ligation of the adapter. This GAT buffer is the same last three bases as the P1 adapter used for the Ion PGM™ sequencing instrument. The information in Table 1 is organized according to the serial number of the barcodes that were generated. The second column shows the key sequence, barcode sequences, and the common C base. The third column shows the barcode sequences and the common C base. The fourth column shows the projection of the combined sequence elements into flowspace. In the table, the bases and flowspace vector elements corresponding to the barcodes are all indicated in bold. In the flowspace mapping, flows 1-8 were assigned to the key sequence, flows 9-18 were assigned to the data digits of the barcode, and flows 19-21 were assigned to the parity digits. Because all the barcodes were followed immediately by a common C base, flow 22 was provided for synchronization. Naturally, such keys, synchronization bases, and/or buffers could be varied.

TABLE 1

Exemplary barcodes and projections into flowspace.

| Serial No. | Key + Barcode + C | Barcode + C | Flowspace Vector |
|---|---|---|---|
| 1 | TCAGTCCTCGAATC<br>(SEQ ID NO: 1) | TCCTCGAATC<br>(SEQ ID NO: 2) | 1010010112100010001211 |

TABLE 1-continued

Exemplary barcodes and projections into flowspace.

| Serial No. | Key + Barcode + C | Barcode + C | Flowspace Vector |
|---|---|---|---|
| 2 | TCAGCTTGCGGATC<br>(SEQ ID NO: 3) | CTTGCGGATC<br>(SEQ ID NO: 4) | 1010010101210010002111 |
| 4 | TCAGTCTAACGGAC<br>(SEQ ID NO: 5) | TCTAACGGAC<br>(SEQ ID NO: 6) | 1010010111102010002101 |
| 5 | TCAGTTCTTAGCGC<br>(SEQ ID NO: 7) | TTCTTAGCGC<br>(SEQ ID NO: 8) | 1010010121201110001001 |
| 6 | TCAGTGAGCGGAAC<br>(SEQ ID NO: 9) | TGAGCGGAAC<br>(SEQ ID NO: 10) | 1010010110011110002201 |
| 7 | TCAGTTAAGCGGTC<br>(SEQ ID NO: 11) | TTAAGCGGTC<br>(SEQ ID NO: 12) | 1010010120002110002011 |
| 9 | TCAGCTGACCGAAC<br>(SEQ ID NO: 13) | CTGACCGAAC<br>(SEQ ID NO: 14) | 1010010101111020001201 |
| 11 | TCAGTCTAGAGGTC<br>(SEQ ID NO: 15) | TCTAGAGGTC<br>(SEQ ID NO: 16) | 1010010111101101002011 |
| 12 | TCAGAAGAGGATTC<br>(SEQ ID NO: 17) | AAGAGGATTC<br>(SEQ ID NO: 18) | 1010010100002101002121 |

According to an embodiment, there is provided a set of barcodes for nucleic acid sequencing, comprising: a plurality of nucleic acid base sequences, each nucleic acid base sequence being a base space representation of a flowspace representation of a codeword of an error-tolerant sample discrimination code. The error-tolerant sample discrimination code may be tolerant to at least two flowspace errors. The error-tolerant sample discrimination code may be an error-correcting code, which may be a ternary Hamming code, or a ternary Golay code, or a ternary tetracode code. The error-tolerant sample discrimination code may be used in various methods to detect flowspace errors (e.g., detect that a particular digit, e.g., "1," for a given flow should be "2") using any suitable error detection algorithm. Although detection may sometimes suffice and correction is not necessarily required, the error-tolerant sample discrimination code may also be used in various methods to correct such detected errors using any suitable error correction algorithm. Such a set of barcodes may be used to distinguish samples based on a flowspace vector obtained during sequencing (e.g., using sequencing-by-synthesis) before making any actual base calls, which may be useful to perform highly rapid and efficient preliminary sample discrimination.

Any suitable decoding algorithms and/or software tools may be used for decoding the flowspace strings read from the barcode sequences to correct and/or detect errors. For example, the decoding can be performed using an exhaustion algorithm in which a damaged codeword is compared to all other members of the code and decoded as the closest matching codeword. If the damaged codeword is equally close to two codewords or is further than half the minimum distance from any codeword, then the algorithm may indicate that an error is detected without making any corrections. In another example, the decoding may involve performing the coding operation in reverse. In another example, the decoding algorithm may use linear algebra techniques to decode the codeword.

A method for sequencing a polynucleotide sample having a barcode sequence, comprising: introducing a series of nucleotides to the polynucleotide sample according to a predetermined flow ordering; obtaining a series of signals resulting from the introducing of nucleotides to the polynucleotide sample; and resolving the series of signals over the barcode sequence to render a flowspace string, wherein the flowspace string is a codeword of an error-tolerant code capable of distinguishing the barcode sequence from other barcode sequences in the presence of one or more errors. In such a method, the error-tolerant code may be an error-correcting code. The error-correcting code may be a ternary code using a three character alphabet. The first character of the alphabet may represent a 0-mer signal, the second character in the alphabet may represent a 1-mer signal, and the third character in the alphabet may represent a 2-mer signal. The ternary code may be a ternary Hamming code. The ternary code may be a ternary Golay code. The codeword may have a length of 15 or fewer characters. The error-correcting code may be capable of correcting up to two errors in the flowspace string. The error-correcting code may be capable of correcting one error in the flowspace string. The barcode sequence may have a length in the range of 5-15 bases. The barcode sequence may have a GC content in the range of 40-60%. The method may further comprise: determining whether the flowspace string contains an error; and correcting the flowspace string if an error is detected. The method may further comprise translating the flowspace string into a base sequence to obtain the sequence of the barcode sequence. The method may further comprise: decoding the flowspace string to the correct flowspace codeword; and translating the flowspace codeword into a base sequence to obtain the sequence of the barcode sequence. The method may further comprise providing multiple different polynucleotide samples for multiplex sequencing by the series of flowed nucleotides, each different polynucleotide sample comprising a different barcode sequence that gives a different flowspace string, each different flowspace string being a different codeword of the error-correcting code. Any two flowspace codewords of the error-correcting code may have a Hamming distance of at least 3. Any two flowspace codewords of the error-correcting code may have a Hamming distance of at least 5. The method may further comprise one or both of: (i) detecting hydrogen ions released by the incorporation of nucleotides into the polynucleotide sample, wherein the amplitude of the signals is related to the amount of hydrogen ions detected, and (ii) detecting inorganic pyrophosphate released by the incorporation of nucleotides into the polynucleotide sample, wherein the amplitude of the signals is related to the amount of inorganic pyrophosphate detected. There is also provided a non-transitory machine-readable storage medium comprising instructions which, when executed by a processor, cause the processor to perform such a method and variants thereof. There is also provided a system, including: a machine-readable memory; and a processor configured to execute machine-readable instructions, which, when executed by the processor, cause the system to perform such a method and variants thereof.

According to an embodiment, there is provided a method of making a polynucleotide, comprising: constructing an error-tolerant code consisting of a set of codewords; translating each codeword to a sample discriminating code sequence for a given nucleotide flow ordering; and obtaining a polynucleotide containing the sample discriminating code sequence. The polynucleotide may be an oligonucleotide that is 5-40 bases in length. The step of obtaining the polynucleotide may comprise synthesizing the polynucleotide. There is also provided a polynucleotide made according to the method comprising: constructing an error-tolerant code consisting of a set of codewords; translating each codeword to a sample discriminating code sequence for a given nucleotide flow ordering; and obtaining a polynucleotide containing the sample discriminating code sequence. The sample discriminating code sequences may be a barcode sequence. The error-tolerant code may be an error-correcting code. The codewords may be translated to barcode sequences for a given nucleotide flow ordering. The error-correcting code, the codewords, and/or the barcode sequences may be designed or selected in any manner described herein. A polynucleotide containing the barcode sequence may be made using any conventional polynucleotide synthesis technique known in the art or can be supplied by commercial sources that provide custom-made polynucleotides of the desired sequence.

According to an exemplary embodiment, there is provided a method for generating sample discriminating code sequences, comprising: constructing an error-tolerant code consisting of a set of codewords; and translating each codeword to a sample discriminating code sequence for a given nucleotide flow ordering. The error-tolerant code may be an error-correcting code. The codewords may be translated to barcode sequences for a given nucleotide flow ordering. The error-correcting code, the codewords, and/or the barcode sequences may be designed or selected in any manner described herein. There is also provided a system for generating sample discriminating code sequences, comprising: a machine-readable memory; and a processor configured to execute machine-readable instructions, which, when executed by the processor, cause the system to perform a method for generating sample discriminating code sequences, comprising: constructing an error-tolerant code consisting of a set of codewords; receiving a predetermined nucleotide flow ordering; and translating each codeword to a sample discriminating code sequence according to the predetermined nucleotide flow ordering. There is also provided a non-transitory machine-readable storage medium comprising instructions which, when executed by a processor, cause the processor to perform a method for generating sample discriminating code sequences, comprising: constructing an error-tolerant code consisting of a set of codewords; receiving a predetermined nucleotide flow ordering; and translating each codeword to a sample discriminating code sequence according to the predetermined nucleotide flow ordering. The sample discriminating code sequences may be a barcode sequence.

According to an exemplary embodiment, there is provided a sequencing kit, comprising: a plurality of different polynucleotides, each different polynucleotide comprising a different molecular sample discriminating code sequence, wherein a flowspace projection of each different molecular sample discriminating code sequence under a flow of a series of nucleotides according to a predetermined flow ordering gives different flowspace strings that are codewords of an error-tolerant code. The plurality of different polynucleotides may include at least 20, 30, 40, 50, 60, 70, 80, 90, 100, or a larger integer of, different polynucleotides. The different molecular sample discriminating code sequences may be different molecular barcode sequences. The sequencing kit may further comprise a polymerase enzyme. The sequencing kit may further comprise multiple containers for holding the different polynucleotides, and each different polynucleotide may be held in a different container. The polynucleotides may be oligonucleotides of 5-40 bases in length. The sequencing kit may further comprise multiple different kinds of nucleotide monomers. The sequencing kit may further comprise a ligase enzyme.

According to an exemplary embodiment, there is provided a sequencing kit, comprising: multiple different polynucleotides (which may be contained in vials, for example), each different polynucleotide comprising a different barcode sequence as described herein. The polynucleotides may be oligonucleotides having 5-40 bases. The sequencing kit may contain at least 16 different polynucleotides, each comprising a different barcode sequence; or at least 32 different polynucleotides; or at least 48 different polynucleotides; or at least 96 different polynucleotides, or more, for example. Each different polynucleotide may be provided in a separate container (e.g., a separate vial). The polynucleotides may be the barcode sequences themselves, or they may further include other elements, such as primer sites, adaptors, ligating sites, linkers, etc. The sequencing kit may also include a set of precursor nucleotide monomers for carrying out sequencing-by-synthesis operations, for example, and/or various other reagents involved in a workflow for preparing and/or sequencing a sample.

According to an exemplary embodiment, there is provided a pool of different polynucleotide strands, each different polynucleotide strand comprising a different barcode sequence; wherein the flowspace projection of each different barcode sequence under a flow of a series of nucleotides according to a predetermined flow ordering gives different flowspace strings that are codewords of an error-tolerant code. The error-tolerant code may be an error-correcting code. The error-correcting code may be a block code. The block code may be a ternary code using a three-character alphabet. The barcode sequence may contain only 1-mer and 2-mer base sequences, and a first character of the alphabet may represent a 0-mer signal, a second character in the alphabet may represent a 1-mer signal, and a third character in the alphabet may represent a 2-mer signal. The block code may be a ternary Golay code. The block code may be a ternary Hamming code. The block code may be a binary code using a two-character alphabet. The barcode sequence may contain only 1-mer bases, and a first character of the alphabet may represent a 0-mer signal, and a second character in the alphabet may represent a 1-mer signal. Each codeword may have a length of 15, 14, 13, 12, 11, 10, or fewer digits. The error-correcting code may be configured to and/or capable of correcting up to two errors in the flowspace string. The error-correcting code may be configured to and/or capable of correcting one error in the flowspace string. The barcode sequences may have a length of 20, 19, 18, 17, 16, 15, 14, 13, 12, 11, 10, or fewer bases. The barcode sequences may have a GC content in the range of 40-60%. The error-correcting code may have a minimum distance of 3. The error-correcting code may have a minimum distance of 5. The polynucleotide pool may be such that any two different flowspace strings for the barcode sequences have a Hamming distance of at least 3. The polynucleotide pool may be such that any two different flowspace strings for the barcode sequences have a Hamming distance of at least 5. The polynucleotide pool may contain at least 96 different polynucleotide strands and the error-correcting code may have at least 96 different codewords.

FIG. 9 illustrates a pool of seven different polynucleotide strands, each associated with a unique barcode sequence. Each polynucleotide strand may have a primer site, a standard key sequence, and a unique barcode sequence. Each polynucleotide strand also may have a different target sequence. Such a pool of polynucleotide strands may be subject to multiplex sequencing and the barcodes (with any read corrections as needed) may help identify the source of the sequence data derived from a multiplex sample.

According to an exemplary embodiment, there is provided a sample identification kit, comprising: a plurality of sample discriminating codes, wherein: a) each sample discriminating code comprises a sequence of individual subunits; b) the sequence of subunits of each sample discriminating code is distinguishable from the sequence of individual subunits of each other member of the plurality of sample discriminating codes; and c) each sample discriminating code is tolerant to one or more errors so as to be discretely resolvable with respect to other sample discriminating codes.

According to an exemplary embodiment, there is provided a sample identification kit, comprising: a plurality of sample discriminating codes, wherein: a) each sample discriminating code comprises a sequence of individual subunits; b) a detectable signal is associated with each subunit or with pairs or sets of subunits such that each sample discriminating code is associated with a sequence of detectable signals; c) each sequence of detectable signals is distinguishable from the sequence of detectable signals of each other member of the plurality of sample discriminating codes; and d) the sequence of detectable signals of each sample discriminating code is tolerant to at least one error so as to be discretely resolvable with respect to other sample discriminating codes.

Figure 10A:
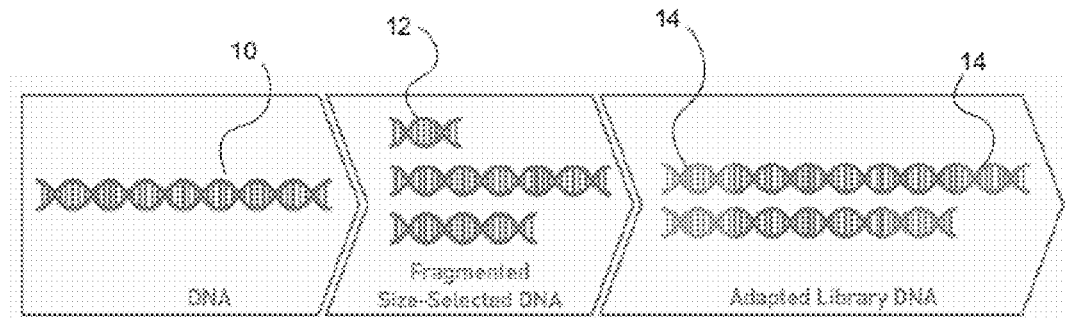
FIGS. 10A-10C illustrate an exemplary workflow for preparing a multiplex sample.
Figure 10B:
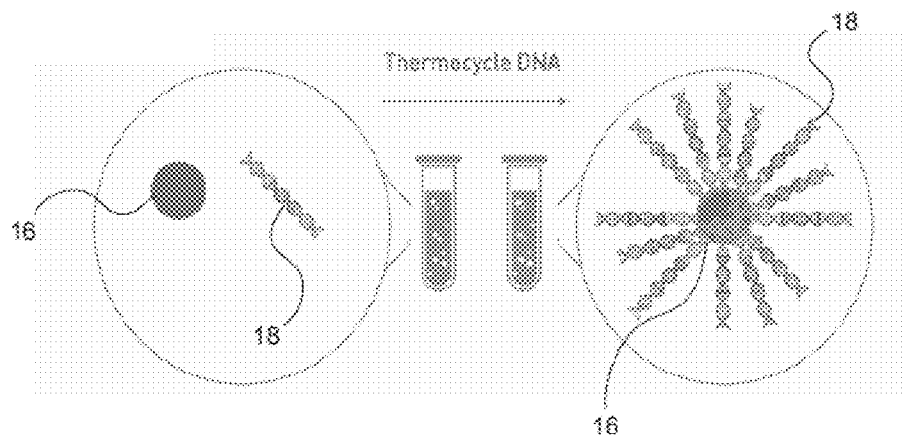
Figure 10C:
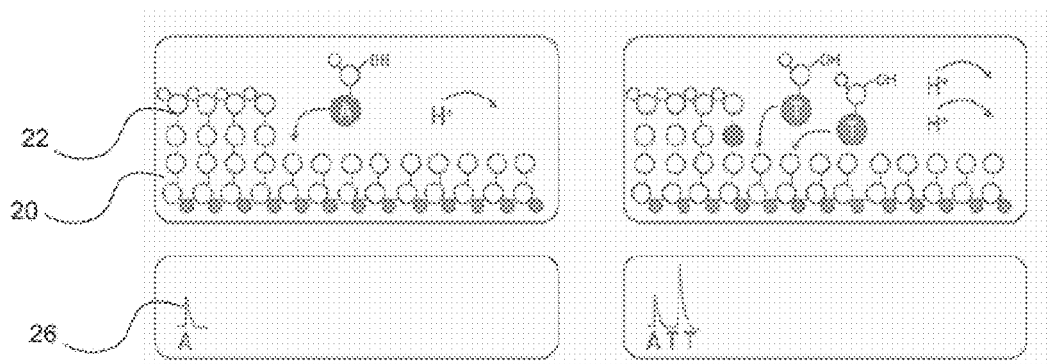

FIGS. 10A-10C illustrate an exemplary workflow for preparing a multiplex sample. FIG. 10A shows an exemplary construction of a genomic DNA fragment library. A bacterial genomic DNA 10 may be fragmented into many DNA fragments 12 using any suitable technique, such as sonication, mechanical shearing, or enzymatic digestion, for example. Platform-specific adaptors 14 may then be ligated onto the ends of the fragments 12. Referring to FIG. 10B, each fragment sample 18 may then be isolated and combined with a bead 16. To allow for identification of the fragment 18, a barcode sequence (not shown in the figure) may be ligated to the fragment 18. The fragment 18 may then be clonally amplified onto the bead 16, resulting in many clonal copies of the fragment 18 on the bead 16. This process may repeated for each different fragment 12 of the library, resulting in many beads, each having the product of a single library fragment 12 amplified many times. Referring to FIG. 10C, the beads 16 may then be loaded onto a microwell array. FIG. 10C shows a partial view of a DNA fragment inside a well as it is undergoing sequencing reactions. A template strand 20 may be paired with a growing complementary strand 22. In the left panel, an A nucleotide is added to the microwell, resulting in a single-base incorporation event, which generates a single hydrogen ion. In the right panel, a T nucleotide is added to the microwell, resulting in a two-base incorporation event, which generates two hydrogen ions. The signal produced by the hydrogen ions are shown as peaks 26 in the ionograms. In various embodiments, a sequencing kit may contain one or more of the materials needed for the above sample preparation and sequencing workflow, including reagents for performing DNA fragmentation, adaptors, primers, ligase enzymes, beads or other solid support, polymerase enzymes, or precursor nucleotide monomers for the incorporation reactions.

According to an exemplary embodiment, there is provided a system, comprising a plurality of identifiable nucleic acid barcodes. The nucleic acid barcodes may be attached to, or associated with, target nucleic acid fragments to form barcoded target fragments. A library of barcoded target fragments may include a plurality of a first barcode attached to target fragments from a first source. Alternatively, a library of barcoded target fragments may include different identifiable barcodes attached to target fragments from different sources to make a multiplex library. For example, a multiplex library may include a mixture of a plurality of a first barcode attached to target fragments from a first source, and a plurality of a second barcode attached to target fragments from a second source. In the multiplex library, the first and second barcodes may be used to identify the source of the first and second target fragments, respectively. Any number of different barcodes may be attached to target fragments from any number of different sources. In a library of barcoded target fragments, the barcode portion may be used to identify: a single target fragment; a single source of the target fragments; a group of target fragments; target fragments from a single source; target fragments from different sources; target fragments from a user-defined group; or any other grouping that may require or benefit from identification. The sequence of the barcoded portion of a barcoded target fragment may be separately read from the target fragment, or read as part of a larger read spanning the barcode and the target fragment. In a sequencing experiment, the nucleic acid barcode may be sequenced with the target fragment and then parsed algorithmically during processing of the sequencing data. In various embodiments, a nucleic acid barcode may comprise a synthetic or natural nucleic acid sequence, DNA, RNA, or other nucleic acids and/or derivatives. For example, a nucleic acid barcode may include nucleotide bases adenine, guanine, cytosine, thymine, uracil, inosine, or analogs thereof. Such barcodes may serve to identify a polynucleotide strand and/or distinguish it from other polynucleotide strands (e.g., those containing a different target sequence of interest), and may be used for various purposes, such as tracking, sorting, and/or identifying the samples, for example. Because different barcodes can be associated with different polynucleotide strands, such barcodes may be useful in multiplexed sequencing of different samples.

Multiplex Libraries

In various embodiments, there are provided sample discriminating codes or barcodes (e.g., nucleic acid barcodes) that may be attached to, or associated with, targets (e.g., nucleic acid fragments) to generate barcoded libraries (e.g., barcoded nucleic acid libraries). Such libraries may be prepared using one or more suitable nucleic acid or biomolecule manipulation procedures, including: fragmenting; size-selecting; end-repairing; tailing; adaptor-joining; nick translation; and purification, for example. In various embodiments, nucleic acid barcodes may be attached to, or associated with, fragments of a target nucleic acid sample using one or more suitable procedure, including ligation, cohesive-end hybridization, nick-translation, primer extension, or amplification, for example. In some embodiments, nucleic acid barcodes may be attached to a target nucleic acid using amplification primers having a particular barcode sequence.

In various embodiments, a target nucleic acid or biomolecule (e.g., proteins, polysaccharides, and nucleic acids, and their polymer subunits, etc.) sample may be isolated from any suitable source, such as solid tissue, tissue, cells, yeast, bacteria, or similar sources, for example. Any suitable methods for isolating samples from such sources may be used. For example, solid tissue or tissue may be weighed, cut, mashed, homogenized, and the sample may be isolated from homogenized samples. An isolated nucleic acid sample may be chromatin, which may be cross-linked with proteins that bind DNA, in a procedure known as ChIP (chromatin immunoprecipitation). In some embodiments, samples may be fragmented using any suitable procedure, including cleaving with an enzyme or chemical, or by shearing. Enzyme cleavage may include any type of restriction endonuclease, endonuclease, or transposase-mediated cleavage.

Fragment Libraries

In various embodiments, there are provided fragment libraries, which may comprise: a first priming site (P1); a second priming site (P2); an insert; an internal adaptor (IA); and a barcode (BC). In some embodiments, a fragment library may include constructs having certain arrangements, such as: a P1 priming site, an insert, an internal adaptor (IA), a barcode (BC), and a P2 priming site. In some embodiments, the fragment library may be attached to a solid support, such as a bead.

Figure 11:
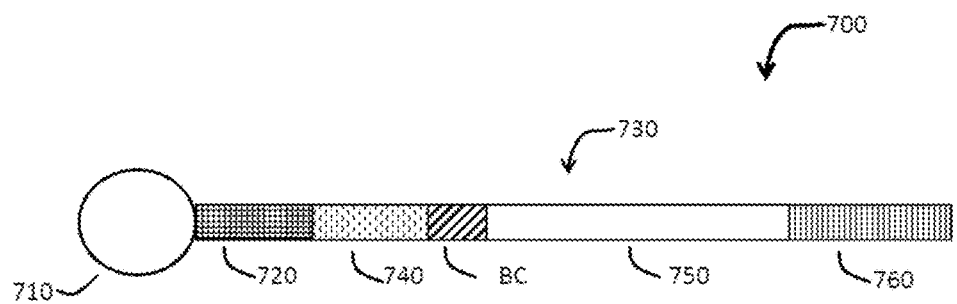
FIG. 11 illustrates an exemplary beaded template.

FIG. 11 illustrates an exemplary beaded template. It shows an exemplary nucleic acid attached to a solid support, such as a bead. A beaded template 700 includes a bead 710 having a linker 720, which is a sequence for attaching a template 730 to the solid support. The template 730 may include a first or P1 priming site 740, an insert 750, and a second or P2 priming site 760. The template 730 may be a synthetic template. The template 730 may be representative of a fragment library. The template 730 may comprise a nucleic acid barcode BC, which may be positioned between the P1 priming site 740 and the insert 750, for example. An internal adaptor may be placed between the P1 priming site 740 and the barcode BC, or between the barcode BC and the insert 750, or between the insert 750 and the P2 priming site 760.

Figure 12:
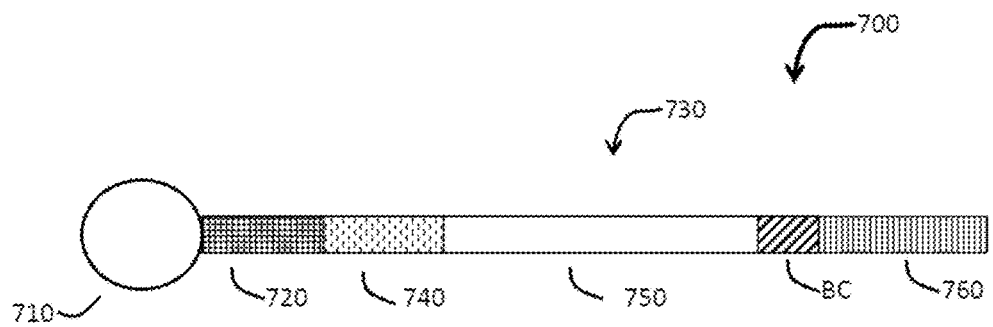
FIG. 12 illustrates another exemplary beaded template.

FIG. 12 illustrates another exemplary beaded template. The nucleic acid barcode BC may be positioned between the insert 750 and the P2 priming site 760. An internal adaptor may be placed between the P1 priming site 740 and the insert 750, or between the insert 750 and the barcode BC, or between the barcode BC and the P2 priming site 760.

In various embodiments, the length of the linker 720 and template 730 may vary. For example, the length of the linker 720 may range from 10 to 100 bases, for example, or from 15 to 45 bases, for example, and may be 18 bases (18 b) in length, for example. The template 730, which comprises the P1 priming site 740, the insert 750, and the P2 priming site 760, may also vary in length. For example, the P1 priming site 740 and the P2 priming site 760 may each range from 10 to 100 bases, for example, or from 15 to 45 bases, for example, and may be 23 bases (23 b) in length, for example. The insert 750 may range from 2 bases (2 b) to 20,000 bases (20 kb), for example, and may be 60 bases (60 b), for example. In an embodiment, the insert 750 may comprise more than 100 bases, such as, e.g., 1,000 or more bases. In various embodiments, the insert may be in the form of a concatenate, in which case, the insert 750 may comprise up to 100,000 bases (100 kb) or more.

In various embodiments, the position of barcode BC may be selected based on various considerations, including the length of the insert, signal-to-noise ratio issues, and/or sequencing bias issues. For example, where signal-to-noise ratio may be an issue (e.g., the signal-to-noise ratio can decrease as additional ligation cycles are performed in sequencing-by-ligation, for example), the barcode BC may be positioned adjacent the P1 priming site 740 to avoid potential errors due to a diminished signal-to-noise ratio, and where the signal-to-noise ratio may not be a significant issue, the barcode BC may be placed adjacent to either the P1 priming site 740 or the P2 priming site 760. In some cases, template sequences may interact differently with a probe sequence used during the sequencing experiment. Placing the barcode BC before the insert 750 can affect the sequencing results for the insert 750. Positioning the barcode BC after the insert 750 can decrease sequencing errors due to bias. Generally, the position of the barcode can be affected by or affect sequencing, and the position that best achieves desired results based on the conditions of the sequencing process may be selected.

In various embodiments, sequencing and decoding of a nucleic acid barcode may be performed with a single forward direction sequence read (e.g., 5'-3' direction along the template), e.g., reading the barcode BC and the insert 750 in a single read. In an embodiment, the forward read may be parsed into the barcode portion and the insert portion algorithmically.

In various embodiments, sample discriminating codes or barcodes may be attached to polymers, such as proteins, and may be a polypeptide attached to a protein. Intein-mediated ligation may join together separate proteins or polypeptides. For example, expressed protein ligation (EPL) involves a native chemical ligation (NCL) reaction between an intein-fusion protein and protein having an N-Cys. In another example, protein trans-splicing involves reconstitution of two halves of an intein protein (see Dawson et al., "Synthesis of proteins by native chemical ligation," Science, 266:776-779 (1994); Muir, "Semisynthesis of Proteins by Expressed Protein Ligation," Ann. Rev. Biochem., 72:249-289 (2003); Paulus, "Protein Splicing and Related Forms of Protein Autoprocessing," Ann. Rev. Biochem., 69:447-496 (2000); and Muralidharan et al., "Protein ligation: an enabling technology for the biophysical analysis of proteins," Nature Methods, 3:429-438 (2006)).

Mate Pair Libraries

Figure 13:
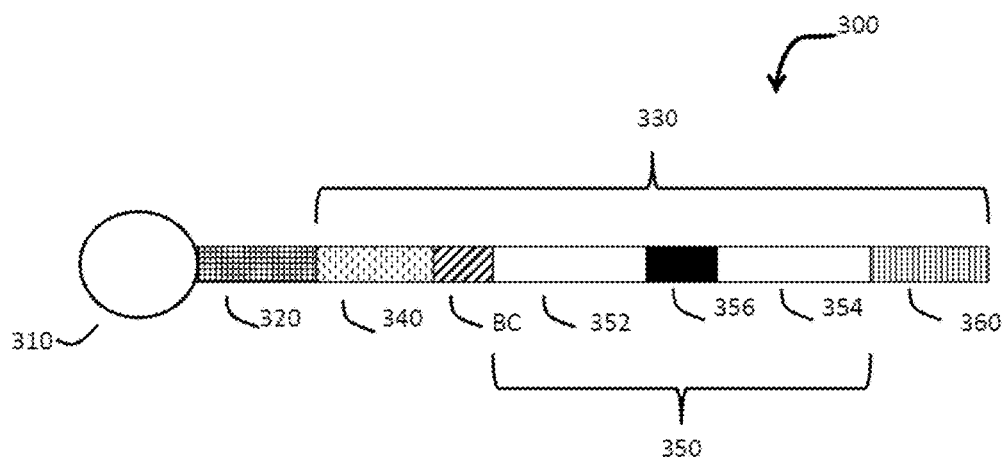
FIG. 13 illustrates an exemplary mate pair beaded template.

In various embodiments, nucleic acid barcodes as described herein may also be used in templates derived from a mate pair library. FIG. 13 illustrates an exemplary mate pair beaded template. It shows a beaded template 300 comprising a bead 310, a linker 320, and a template 330. The template 330 may comprise a first or P1 priming site 340 and second or P2 priming site 360, each of which may range in length from 10 to 100 bases, for example, or from 15 to 45 bases, for example, and may be 23 bases in length, for example. The template 330 may further comprise an insert 350, which may comprise a first tag sequence 352, a second tag sequence 354, and an internal adapter 356 located between the first and second tag sequences 352 and 354. In various embodiments, the barcode BC may be placed between the second tag sequence 354 and the P2 priming site 360. Other positions are possible. The first and second tag sequences 352 and 354 may each have a length ranging from 2 bases (2 b) to 20,000 bases (20 kb), for example, and may have a length of 60 bases, for example; they may be the same sequence or different sequences; and they may comprise a different number of bases or the same number of bases. The internal adapter 356, which may be common to all of the template sequences, may have a length ranging from 10 to 100 bases, for example, or from 15 to 45 bases, for example, and may have a length of 36 bases, for example.

In various embodiments, the barcode BC may be positioned based on the conditions of the sequencing process. For example, the barcode BC may be positioned between the P1 priming site 340 and a first tag sequence 352, as shown in FIG. 13, or between a second tag sequence 354 and the P2 priming site 360. Alternatively, the barcode BC may be positioned adjacent an internal adapter 356 and either a first tag sequence 352 or a second tag sequence 354. In another embodiment, the barcode BC may be integrated within an internal adapter 356.

In various embodiments, nucleic acid barcodes as described herein may be incorporated into an extended oligonucleotide comprising the barcode and one or more of a P1 primer, a P2 primer, and an internal adapter. For example, the barcode may be incorporated into an oligonucleotide comprising the P2 primer, the barcode, and an internal adapter, which may allow the barcode to be sequenced in a separate read. In various embodiments, the barcode may be incorporated into other oligonucleotides or arrangements of oligonucleotides.

In various embodiments, nucleic acid barcodes as described herein may be added to libraries using any suitable method. For example, full-length double-stranded oligonucleotide pairs specific for each barcode may be annealed and ligated onto double-stranded nucleic acid fragments. In another example, one full-length double-stranded oligonucleotide may be annealed to one short universal oligonucleotide specific for each barcode and ligated onto double-stranded nucleic acid fragments. In a further example, a universal oligonucleotide adapter may be ligated onto single-stranded RNA, converted into double-stranded DNA, and the barcode may be added using a barcode-specific PCR primer during library amplification.

In various embodiments, nucleic acid barcodes as described herein may be adapted for use in generating mate pair libraries for nucleic acid sequencing. For example, the barcodes may be used in SOLiD® Mate-Paired Library Construction Kits by Applied Biosystems (now Life Technologies Corp.). In various embodiments, the P2 adaptor may be replaced with a multiplex adaptor having three portions: an internal primer binding sequence; a barcode sequence; and a P2 primer binding sequence.

In an embodiment, the first tag sequence 352 may be a first sheared DNA tag sequence and the second tag sequence 354 may be a second sheared DNA tag sequence 354. Because the internal adaptor sequence may be located in between the two tag sequences 352 and 354, an alternative sequence may be used to prime the sequencing of the barcode BC.

According to an embodiment, there is provided a method for constructing a mate pair library using one or more barcodes as described herein positioned adjacent a P2 primer, comprising the following steps (which may be performed in addition to other routine library creation steps known to those ordinarily skilled in the art): (1) generating DNA fragments by shearing a DNA sample and repairing the ends; (2) ligating LMP CAP adaptors to the ends of the fragmented DNA; (3) circularizing the DNA with an internal adaptor which leaves nicks; (4) conducting a nick translation reaction to move the position of the nicks to a new position that is within the DNA fragment (the timing of the nick translation reaction may be stopped to place the nick at any desired position along the DNA fragment); (5) digesting the nick translated DNA with T7 exonuclease and S1 nuclease to release the linear, double-stranded mate pair tags; and (6) ligating multiplex P1 and P2 barcoded adaptors to the mate pair tags.

In an embodiment, such a mate pair library may be amplified, quantitated by qPCR or other method, and/or pooled. In various embodiments, beads may be templated with the mate pair library by emulsion PCR, and the resulting beads may be sequenced. In such a library, the P1 and IA end of the insert sequences and the barcode may be sequenced in three separate reads from the same strand. The barcode may be sequenced using barcode adaptor sequences having P2, barcode, and priming sequences. Any suitable priming sequences may be used.

Paired End Libraries

In various embodiments, nucleic acid barcodes as described herein may be adapted for use in generating paired end libraries. Generally, paired end libraries may be constructed by: fragmenting a starting source of DNA (e.g., shearing); and attaching P1 adaptors and barcoded P2 adaptors to the ends of the fragments. The paired end library may be amplified and sequenced. In an embodiment, the paired ends and the barcodes in the paired end library may be sequenced in separate reads from the same strand.

SAGE™ Libraries

In various embodiments, nucleic acid barcodes as described herein may be adapted to construct a nucleic acid library for use in gene expression analysis using nucleic acid sequencing. For example, the nucleic acid barcodes may be used in SOLiD® SAGE™ gene expression analysis (where SAGE™ is Serial Analysis of Gene Expression, developed by Applied Biosystems (now Life Technologies Corp.)).

In various embodiments, nucleic acid barcodes as described herein may be designed to lack one or more restriction enzyme recognition sequence(s), amplification sequences, or adaptor sequences that are used for constructing the nucleic acid library. For example, in SAGE™, a recognition site for the restriction enzyme EcoP15I is used to generate SAGE™ tags. Nucleic acid barcodes used in SAGE™, other gene expression analysis, or other analyses reliant on recognition sites for restriction enzymes, for example, may be designed to avoid recognition sites necessary for the further analysis carried out in those processes.

In various embodiments, SAGE™-compatible nucleic acid barcodes may be designed to be positioned adjacent the P1 primer. SAGE™ tags have a 2-base overhang resulting from EcoP15I cleavage. To account for the overhang, the nucleic acid barcode may comprise an overhang end having 1, 2, 3, 4, 5, or longer overhang end. The overhang end may include a degenerate sequence. The nucleic acid barcode may include a 2-nucleotide degenerate extension to ligate to the SAGE™ tag. Alternatively, the 2-base overhang on the SAGE™ tag may be degraded or filled-in to produce a blunt end for ligating to the nucleic acid barcode.

Figure 14A:
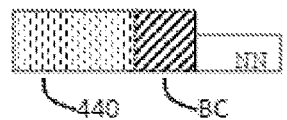
FIG. 14A illustrates an exemplary barcoded adaptor.
Figure 14B:
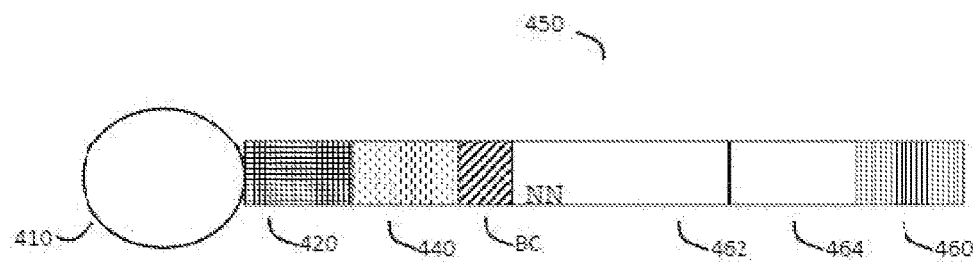
FIG. 14B illustrates an exemplary beaded template.

FIG. 14A illustrates an exemplary barcoded adaptor. It shows a barcode BC attached to a P1 primer 440, wherein the barcode BC comprises a 2-nucleotide degenerate extension NN. A P2 primer may be adapted to ligate properly to the SAGE™ tag. The P2 primer may have an NlaIII overhang (GTAC) attached to an EcoP15I recognition site to ligate to the SAGE™ tag. FIG. 14B illustrates an exemplary beaded template. It shows a SAGE™ tag 450 ligated to barcode BC and the NlaIII overhang 462 and EcoP15I recognition site 464, which are ligated to P2 primer 460. P1 primer 440 is attached to solid support 410 (e.g., bead) through linker 420.

Figure 15:
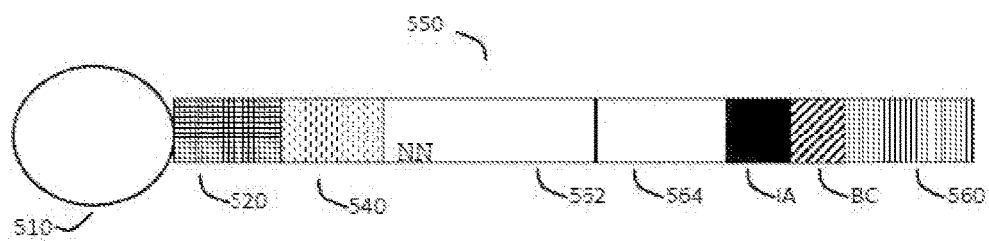
FIG. 15 illustrates another exemplary beaded template.

FIG. 15 illustrates another exemplary beaded template. It shows a barcode BC positioned adjacent a P2 primer 560. Primer P1 540 is attached to a solid support 510 (e.g., a bead) through linker 520. A 2-nucleotide degenerate overhang NN allows a SAGE™ tag 550 to ligate to the P1 primer 540. On the other side of the SAGE™ tag 550, an internal adapter IA is ligated to an EcoP15I recognition site 564 and an NlaIII overhang 562. The barcode may be incorporated in an oligonucleotide comprising one or more oligonucleotide sequences, such as, e.g., an internal adapter and a P2 primer, or comprising a modified internal adapter, the barcode, and a P2 primer. In various embodiments, the barcode need not be part of the library construct, but can be introduced by PCR amplification using a primer having the barcode sequence.

According to an embodiment, there is provided a method for generating barcoded SAGE™ libraries using one or more barcodes as described herein positioned adjacent the P2 primer, comprising the following steps (which may be performed in addition to other routine library creation steps known to those ordinarily skilled in the art): (1) generating an immobilized cDNA library from poly-A RNA; (2) digesting the cDNA with a restriction enzyme to create cohesive ends for EcoP15I ends (e.g., digesting with Nla III); (3) ligating to the Nla III cut ends an internal adaptor having cohesive ends for EcoP15I to form an EcoP15I recognition site; (4) cleaving the EcoP15I site to generate SAGE™ tag fragments; (5) ligating P1 adaptors (e.g., SAGE™-specific P1 adaptors have a 2-base degenerate extension to hybridize with the overhang from the cleaved EcoP15I ends); and (6) amplifying the library (e.g., PCR using primers having a P2 adaptor and barcode sequences). Any suitable primers may be used.

In various embodiments, such a library may be amplified, quantitated by qPCR or other method, and/or pooled. In various embodiments, beads may be templated with the SAGE™ library by emulsion PCR, and the templated beads may be sequenced.

Yeast Libraries

In various embodiments, nucleic acid barcodes as described herein may be used in combination with other yeast barcodes, including those described in Yan et al., "Yeast Barcoders: a chemogenomic application of a universal donor-strain collection carrying bar-code identifiers," Nature Methods, 5(8):719-725 (2008), for example, which is incorporated by reference herein in its entirety. Yeast barcodes may be unique sequences identifying about 6,000 *S. cerevisiae* gene deletion strains, and may comprise a signature sequence of about 20 bases flanked by conserved PCR primer sequences. In an embodiment, a set of barcodes comprising about 100 uniquely identifiable barcodes as described herein may be used in combination with 6,000 other yeast barcodes to yield about 600,000 targets to be analyzed (e.g., per location on a slide when using a SOLiD® sequencing platform or using some other support, e.g., an Ion PGM™ or Ion Proton™ chip and sequencing platform, for example). For example, a SOLiD® slide would provide capacity for about 4.8 million targets, and using both slides in a SOLiD® apparatus would allow about 9.6 million targets to be analyzed simultaneously. Many more targets could be analyzed simultaneously using Ion PGM™ 314™, 316™, or 318™ Chips (which have about 1, 6, and 11 million wells, respectively), an Ion Proton™ Chip (which is expected to have about 165 million wells), and/or an Ion Proton™ II Chip (which is expected to have about 660 million wells). In an embodiment, a sequencing experiment may be performed in which chemical compounds are tested against each of the 6,000 *S. cerevisiae* gene deletion strains. Each chemical compound may be identified by a uniquely identifiable barcode as described herein, and each of the 6,000 *S. cerevisiae* gene deletion strains may be identified by a uniquely identifiable yeast barcode.

In various embodiments, nucleic acid barcodes as described herein may be combined with at least one yeast barcode to prepare a module to be analyzed. The module may comprise a first conserved PCR primer adjacent a P1 primer. The nucleic acid barcode may be ligated to a P2 primer between the P2 primer and a second conserved PCR primer. An internal adapter may be positioned between the nucleic acid barcode and the second conserved PCR primer. In an embodiment, the complete nucleic acid sequence may comprise a P1 primer, a first conserved PCR primer, an insert with a yeast barcode, a second conserved PCR primer, an internal adapter, a nucleic acid barcode as described herein, and a P2 primer. Any suitable primers may be used.

ChIP-Seq Libraries

In various embodiments, nucleic acid barcodes as described herein may be adapted for use in Chromatin immunoprecipitation (ChIP) sequencing to generate ChIP-based libraries. ChIP involves isolating genomic nucleic acids that are associated with DNA-binding proteins. Chromatin/protein complexes may be isolated using a SOLiD® ChIP-Seq Kit from Applied Biosystems (now part of Life Technologies Corp.). Isolated chromatin/protein complexes can be manipulated and ligated to nucleic acid barcodes and related adaptors to construct a ChIP-based library. General steps for ChIP include: (1) treating live cells or tissue with formaldehyde to crosslink proximal molecules to create protein/DNA complexes; (2) lysing the cells to release the cross-linked complexes; (3) fragmenting the DNA (e.g., via sonication); (4) immunoprecipitating the protein/DNA complex of interest using certain antibodies conjugated to beads; (5) releasing the DNA from the cross-linked complex by heat treatment; and (6) purifying the released DNA. General steps for preparing a ChIP-based library include: (1) generating cohesive ends on the ChIP-isolated DNA (e.g., end-repair); and (2) attaching P1, P2 and/or coded adaptors (e.g., with nucleic acid barcodes) to the ends of the ChIP-isolated DNA. Nick translation can be performed on the adaptor-ligated DNA to close any gaps or nicks between the DNA fragment and the adaptors. The ChIP-based library may include fragments of chromatin ligated at the ends with any combination of P1, P2, and/or coded adaptors (e.g., with nucleic acid barcodes).

According to various embodiments, one or more features of any one or more of the above-discussed teachings and/or embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various embodiments, one or more features of any one or more of the above-discussed teachings and/or embodiments may be performed or implemented using appropriately configured and/or programmed non-transitory machine-readable medium or article that may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and nonvolatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various embodiments, one or more features of any one or more of the above-discussed teachings and/or embodiments may be performed or implemented at least partly using a distributed, clustered, remote, or cloud computing resource.

According to various embodiments, one or more features of any one or more of the above-discussed teachings and/or embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, Pascal, Basic, Fortran, Cobol, Perl, Java, and Ada.

According to various embodiments, one or more of the above-discussed embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

Various other embodiments may be derived by repeating, adding, or substituting any generically or specifically described features and/or components and/or substances and/or steps and/or operating conditions set forth in one or more of the above-described embodiments. Further, it should be understood that an order of steps or order for performing certain actions is immaterial so long as the objective of the steps or action remains achievable, unless specifically stated otherwise. Furthermore, two or more steps or actions can be conducted simultaneously so long as the objective of the steps or action remains achievable, unless specifically stated otherwise. Moreover, any one or more feature, component, aspect, step, or other characteristic mentioned in one of the above-discussed embodiments may be considered to be a potential optional feature, component, aspect, step, or other characteristic of any other of the above-discussed embodiments so long as the objective of such any other of the above-discussed embodiments remains achievable, unless specifically stated otherwise.

Although various embodiments of the present teachings may advantageously be used with sequencing-by-synthesis approaches, as described herein and in Rothberg et al., U.S. Pat. Publ. No. 2009/0026082; Anderson et al., SENSORS AND ACTUATORS B CHEM., 129:79-86 (2008); Pourmand et al., PROC. NATl. ACAD. SCI., 103:6466-6470 (2006), which are all incorporated by reference herein in their entirety, for example, the present teachings may also be used with other approaches, such as variants of sequencing-by-synthesis including methods where the nucleotides or nucleoside triphosphate precursors are modified to be reversible terminators (sometimes referred to as cyclic reversible termination (CRT) methods) and methods where the nucleotides or nucleoside triphosphate precursors are unmodified (sometimes referred to as cyclic single base delivery (CSD) methods), for example, or more generally methods that comprise repeated steps of delivering (or extending in response to delivering) nucleotides (to the polymerase-primer-template complex) and collecting signals (or detecting the incorporation either directly or indirectly).

Although various embodiments of the present teachings may advantageously be used in connection with pH-based sequence detection, as described herein and in Rothberg et al., U.S. Pat. Appl. Publ. Nos. 2009/0127589 and 2009/0026082 and Rothberg et al., U.K. Pat. Appl. Publ. No. GB2461127, which are all incorporated by reference herein in their entirety, for example, the present teachings may also be used with other detection approaches, including the detection of pyrophosphate (PPi) released by the incorporation reaction (see, e.g., U.S. Pat. Nos. 6,210,891; 6,258,568; and 6,828,100); various fluorescence-based sequencing instrumentation (see, e.g., U.S. Pat. Nos. 7,211,390; 7,244,559; and 7,264,929); some sequencing-by-synthesis techniques that can detect labels associated with the nucleotides, such as mass tags, fluorescent, and/or chemiluminescent labels (in which case an inactivation step may be included in the workflow (e.g., by chemical cleavage or photobleaching) prior to the next cycle of synthesis and detection)); and more generally methods where an incorporation reaction generates or results in a product or constituent with a property capable of being monitored and used to detect the incorporation event, including, for example, changes in magnitude (e.g., heat) or concentration (e.g., pyrophosphate and/or hydrogen ions), and signal (e.g., fluorescence, chemiluminescence, light generation), in which cases the amount of the detected product or constituent may be monotonically related to the number of incorporation events, for example.

The following documents are all incorporated by reference herein in their entirety: Li et al., International Publ. No. WO/2012/044847, published Apr. 5, 2012; Chen et al., U.S. patent application Ser. No. 13/482,542, filed May 29, 2012; Fu et al., "Counting individual DNA molecules by the stochastic attachment of diverse labels," PNAS 108(22): 9026-9031 (May 31, 2011); and Shiroguchi et al., "Digital RNA sequencing minimizes sequence-dependent bias and amplification noise with optimized single-molecule barcodes," PNAS 109(4):1347-1352 (Jan. 24, 2012).

Although the present description described in detail certain embodiments, other embodiments are also possible and within the scope of the present invention. For example, those skilled in the art may appreciate from the present description that the present teachings may be implemented in a variety of forms, and that the various embodiments may be implemented alone or in combination. Variations and modifications will be apparent to those skilled in the art from consideration of the specification and figures and practice of the teachings described in the specification and figures, and the claims.

The invention claimed is:

1. A method for sequencing a polynucleotide, the method comprising:

introducing, into a polynucleotide, a barcode sequence to create a polynucleotide sample, wherein the barcode sequence is a series of nucleotide bases determined by a predetermined flowspace vector corresponding to a predetermined order of nucleotide flows used for sequencing, wherein the predetermined flowspace vector is a string of characters with each character representing an expected number of nucleotide incorporations resulting from a nucleotide flow of the predetermined order of nucleotide flows;

inserting the created polynucleotide sample into a flow chamber of a sequencing instrument comprising the flow chamber, a sensor in the flow chamber, and a fluidics controller configured to control the flow of nucleotides into the flow chamber;

exposing the created polynucleotide sample in the flow chamber to the series of nucleotides in a presence of a polymerase and a primer by individually flowing the series of nucleotides into the flow chamber according to the predetermined order of nucleotide flows using the fluidics controller, wherein incorporation of nucleotides of the series of nucleotides into the created polynucleotide sample produces a synthesized polynucleotide complementary to the polynucleotide sample;

obtaining, using the sensor, a series of signals resulting from the exposing of the created polynucleotide sample to the series of nucleotides, the series of signals indicating one or more nucleotide incorporations or one or more nucleotide non-incorporations for each nucleotide flow;

outputting the series of signals as data to a computing unit in communication with the sensor, the computing unit comprising a processor and a memory configured to receive and store the data;

resolving, using the processor, the series of signals to generate a rendered flowspace string of characters, wherein each character represents a number of nucleotide incorporations resulting from a respective nucleotide flow of the predetermined order of nucleotide flows;

comparing, using the processor, the rendered flowspace string of characters to predetermined flowspace strings of characters corresponding to a set of barcode sequences comprising the introduced barcode sequence, wherein the predetermined flowspace strings of characters are codewords of an error-tolerant code, the error-tolerant code is an error-correcting code configured to correct one or more errors present in the rendered flowspace string of characters based on differences between the rendered flowspace string and the predetermined flowspace strings of characters; and identifying, by the processor, the polynucleotide of the polynucleotide sample based on the comparison.

2. The method of claim 1, wherein the error-correcting code is a ternary code using a three character alphabet.

3. The method of claim 2, wherein a first character of the alphabet represents a 0-mer signal, a second character in the alphabet represents a 1-mer signal, and a third character in the alphabet represents a 2-mer signal.

4. The method of claim 2, wherein the ternary code is a ternary Hamming code.

5. The method of claim 2, wherein the ternary code is a ternary Golay code.

6. The method of claim 1, wherein the rendered flowspace string of characters has a length of 15 or fewer characters.

7. The method of claim 1, wherein the error-correcting code is capable of correcting up to two errors in the rendered flowspace string of characters.

8. The method of claim 1, wherein the error-correcting code is capable of correcting three or more errors in the rendered flowspace string of characters.

9. The method of claim 1, wherein the barcode sequence has a length in a range of 5-15 bases.

10. The method of claim 1, further comprising determining whether the rendered flowspace string of characters contains an error based on the differences between the rendered flowspace string of characters and the predetermined flowspace strings of characters.

11. The method of claim 10, further comprising correcting the rendered flowspace string of characters if the rendered flowspace string of characters is determined to contain an error.

12. The method of claim 11, further comprising translating the rendered flowspace string of characters into a base sequence.

13. The method of claim 1, further comprising:
  decoding the rendered flowspace string of characters to one of the codewords of the error-correcting code; and
  translating the codeword into a base sequence.

14. The method of claim 1, further comprising providing multiple different polynucleotide samples for multiplex sequencing by the exposing to the series of nucleotides, each different polynucleotide sample comprising a different barcode sequence from the set of barcode sequences.

15. The method of claim 14, wherein any two codewords of the error-correcting code have a minimal Hamming distance of 3.

16. The method of claim 14, wherein any two codewords of the error-correcting code have a minimal Hamming distance of 5.

17. The method of claim 1, wherein obtaining the series of signals further comprises at least one of: (i) detecting hydrogen ions released by the incorporation of nucleotides into the polynucleotide sample, wherein an amplitude of the signals is related to an amount of hydrogen ions detected, and (ii) detecting inorganic pyrophosphate released by incorporation of nucleotides into the polynucleotide sample, wherein an amplitude of the signals is related to an amount of inorganic pyrophosphate detected.

18. A system comprising:
  a sequencing instrument comprising:
    a flow chamber configured to receive a polynucleotide sample, a polymerase, and a primer, the polynucleotide sample comprising a polynucleotide incorporating a barcode sequence, wherein the barcode sequence is a series of nucleotide bases determined by a predetermined flowspace vector corresponding to a predetermined order of nucleotide flows used for sequencing, wherein the predetermined flowspace vector is a string of characters with each character representing an expected number of nucleotide incorporations resulting from a nucleotide flow of the predetermined order of nucleotide flows;
    a fluidics controller configured to flow nucleotides into the flow chamber to expose the polynucleotide sample to a series of nucleotides by individually flowing the series of nucleotides according to the predetermined order of nucleotide flows, and
    a sensor configured to obtain a series of signals resulting from the exposing of the polynucleotide sample to the series of nucleotides, and output the series of signals as data, the series of signals indicating one or more nucleotide incorporations or one or more nucleotide non-incorporations for each nucleotide flow; and
  a computing unit in communication with the sensor, the computing unit comprising a processor and a memory configured to receive and store the data, the processor configured to:
    resolve the series of signals to generate a rendered flowspace string of characters, wherein each character represents a number of nucleotide incorporations resulting from a respective nucleotide flow of the predetermined order of nucleotide flows;
    compare the rendered flowspace string of characters to predetermined flowspace strings of characters corresponding to a set of barcode sequences comprising the incorporated barcode sequence, wherein the predetermined flowspace strings of characters are codewords of an error-tolerant code, the error-tolerant code is an error-correcting code configured to correct one or more errors present in the rendered flowspace string of characters based on differences between the rendered flowspace string of characters and the predetermined flowspace strings of characters; and
    identify the polynucleotide of the polynucleotide sample based on the comparison.

19. The method of claim 1, wherein the sequencing instrument comprises the computing unit.

20. The system of claim 18, wherein the sequencing instrument comprises the computing unit.

* * * * *

UNITED STATES PATENT AND TRADEMARK OFFICE
CERTIFICATE OF CORRECTION

| | |
|---|---|
| PATENT NO. | : 10,704,164 B2 |
| APPLICATION NO. | : 13/599876 |
| DATED | : July 7, 2020 |
| INVENTOR(S) | : Hubbell |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 732 days.

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 18

<210> SEQ ID NO 1
<211> LENGTH: 14
<212> TYPE: DNA
<213> ORGANISM: Artificial Sequence
<220> FEATURE:
<223> OTHER INFORMATION: Sequence Including Exemplary Barcode

<400> SEQUENCE: 1
tcagtcctcg aatc                                                        14

<210> SEQ ID NO 2
<211> LENGTH: 10
<212> TYPE: DNA
<213> ORGANISM: Artificial Sequence
```

```
<220> FEATURE:
<223> OTHER INFORMATION: Sequence Including Exemplary Barcode

<400> SEQUENCE: 2
tcctcgaatc                                                          10

<210> SEQ ID NO 3
<211> LENGTH: 14
<212> TYPE: DNA
<213> ORGANISM: Artificial Sequence
<220> FEATURE:
<223> OTHER INFORMATION: Sequence Including Exemplary Barcode

<400> SEQUENCE: 3
tcagcttgcg gatc                                                     14

<210> SEQ ID NO 4
<211> LENGTH: 10
<212> TYPE: DNA
<213> ORGANISM: Artificial Sequence
<220> FEATURE:
<223> OTHER INFORMATION: Sequence Including Exemplary Barcode

<400> SEQUENCE: 4
cttgcggatc                                                          10

<210> SEQ ID NO 5
<211> LENGTH: 14
<212> TYPE: DNA
<213> ORGANISM: Artificial Sequence
<220> FEATURE:
<223> OTHER INFORMATION: Sequence Including Exemplary Barcode

<400> SEQUENCE: 5
tcagtctaac ggac                                                     14

<210> SEQ ID NO 6
<211> LENGTH: 10
<212> TYPE: DNA
<213> ORGANISM: Artificial Sequence
<220> FEATURE:
<223> OTHER INFORMATION: Sequence Including Exemplary Barcode

<400> SEQUENCE: 6
tctaacggac                                                          10

<210> SEQ ID NO 7
<211> LENGTH: 14
<212> TYPE: DNA
<213> ORGANISM: Artificial Sequence
<220> FEATURE:
<223> OTHER INFORMATION: Sequence Including Exemplary Barcode

<400> SEQUENCE: 7
tcagttctta gcgc                                                     14

<210> SEQ ID NO 8
<211> LENGTH: 10
<212> TYPE: DNA
<213> ORGANISM: Artificial Sequence
<220> FEATURE:
<223> OTHER INFORMATION: Sequence Including Exemplary Barcode

<400> SEQUENCE: 8
ttcttagcgc                                                          10
```

```
<210> SEQ ID NO 9
<211> LENGTH: 14
<212> TYPE: DNA
<213> ORGANISM: Artificial Sequence
<220> FEATURE:
<223> OTHER INFORMATION: Sequence Including Exemplary Barcode

<400> SEQUENCE: 9
tcagtgagcg gaac                                                        14

<210> SEQ ID NO 10
<211> LENGTH: 10
<212> TYPE: DNA
<213> ORGANISM: Artificial Sequence
<220> FEATURE:
<223> OTHER INFORMATION: Sequence Including Exemplary Barcode

<400> SEQUENCE: 10
tgagcggaac                                                             10

<210> SEQ ID NO 11
<211> LENGTH: 14
<212> TYPE: DNA
<213> ORGANISM: Artificial Sequence
<220> FEATURE:
<223> OTHER INFORMATION: Sequence Including Exemplary Barcode

<400> SEQUENCE: 11
tcagttaagc ggtc                                                        14

<210> SEQ ID NO 12
<211> LENGTH: 10
<212> TYPE: DNA
<213> ORGANISM: Artificial Sequence
<220> FEATURE:
<223> OTHER INFORMATION: Sequence Including Exemplary Barcode

<400> SEQUENCE: 12
ttaagcggtc                                                             10

<210> SEQ ID NO 13
<211> LENGTH: 14
<212> TYPE: DNA
<213> ORGANISM: Artificial Sequence
<220> FEATURE:
<223> OTHER INFORMATION: Sequence Including Exemplary Barcode

<400> SEQUENCE: 13
tcagctgacc gaac                                                        14

<210> SEQ ID NO 14
<211> LENGTH: 10
<212> TYPE: DNA
<213> ORGANISM: Artificial Sequence
<220> FEATURE:
<223> OTHER INFORMATION: Sequence Including Exemplary Barcode

<400> SEQUENCE: 14
ctgaccgaac                                                             10

<210> SEQ ID NO 15
<211> LENGTH: 14
<212> TYPE: DNA
<213> ORGANISM: Artificial Sequence
<220> FEATURE:
<223> OTHER INFORMATION: Sequence Including Exemplary Barcode
```

```
<400> SEQUENCE: 15
tcagtctaga ggtc                                                              14

<210> SEQ ID NO 16
<211> LENGTH: 10
<212> TYPE: DNA
<213> ORGANISM: Artificial Sequence
<220> FEATURE:
<223> OTHER INFORMATION: Sequence Including Exemplary Barcode

<400> SEQUENCE: 16
tctagaggtc                                                                   10

<210> SEQ ID NO 17
<211> LENGTH: 14
<212> TYPE: DNA
<213> ORGANISM: Artificial Sequence
<220> FEATURE:
<223> OTHER INFORMATION: Sequence Including Exemplary Barcode

<400> SEQUENCE: 17
tcagaagagg attc                                                              14

<210> SEQ ID NO 18
<211> LENGTH: 10
<212> TYPE: DNA
<213> ORGANISM: Artificial Sequence
<220> FEATURE:
<223> OTHER INFORMATION: Sequence Including Exemplary Barcode

<400> SEQUENCE: 18
aagaggattc                                                                   10
```